(12) United States Patent
Katakura et al.

(10) Patent No.: US 8,242,488 B2
(45) Date of Patent: Aug. 14, 2012

(54) ORGANIC ELECTROLUMINESCENT ELEMENT, DISPLAY DEVICE, AND ILLUMINATING DEVICE

(75) Inventors: Rie Katakura, Tokyo (JP); Hiroshi Kita, Tokyo (JP); Hideo Taka, Tokyo (JP)

(73) Assignee: Konica Minolta Holdings, Inc., Tokyo (JP)

( * ) Notice: Subject to any disclaimer, the term of this patent is extended or adjusted under 35 U.S.C. 154(b) by 175 days.

(21) Appl. No.: 12/601,542

(22) PCT Filed: May 28, 2008

(86) PCT No.: PCT/JP2008/059805
§ 371 (c)(1),
(2), (4) Date: Nov. 24, 2009

(87) PCT Pub. No.: WO2008/146838
PCT Pub. Date: Dec. 4, 2008

(65) Prior Publication Data
US 2010/0207105 A1    Aug. 19, 2010

(30) Foreign Application Priority Data
May 30, 2007    (JP) .................................. 2007-143049

(51) Int. Cl.
*H01L 51/54* (2006.01)
(52) U.S. Cl. ...... 257/40; 257/98; 257/101; 257/E51.026
(58) Field of Classification Search .................. 257/40, 257/98, 101, E51.026; 438/82, 99
See application file for complete search history.

(56) References Cited

U.S. PATENT DOCUMENTS
2006/0175957 A1*  8/2006  Suzuri et al. .................. 313/504

FOREIGN PATENT DOCUMENTS

| JP | 5271166 | 10/1993 |
|---|---|---|
| JP | 2001297882 | 10/2001 |
| JP | 2003073666 | 3/2003 |
| JP | 2003086371 | 3/2003 |
| JP | 200593159 | 4/2005 |
| JP | 2005519429 | 6/2005 |
| JP | 2006237306 A * | 9/2006 |
| JP | 200712510 | 1/2007 |
| WO | 2005009088 | 1/2005 |

OTHER PUBLICATIONS

Otsu et al., Machine Translation of JP Pub. 2006-237306 A.*

* cited by examiner

*Primary Examiner* — Lynne Gurley
*Assistant Examiner* — Vernon P Webb
(74) *Attorney, Agent, or Firm* — Lucas & Mercanti, LLP

(57) ABSTRACT

Disclosed is an organic electroluminescent device having high external quantum efficiency and long emission life and an illuminating device and a display device, each comprising the organic electroluminescent device. The organic electroluminescent device comprises at least an anode and a cathode arranged on a supporting substrate and at least two organic layers, namely a first layer and a second layer, between the anode and the cathode, in which the organic electroluminescent device is characterized in that the first organic layer contains a light emitting dopant and the second organic layer contains a charge-transporting material and a part of the material constituting the first organic layer, and the second organic layer is formed by coating after formation of the first organic layer.

15 Claims, 1 Drawing Sheet

ORGANIC ELECTROLUMINESCENT ELEMENT, DISPLAY DEVICE, AND ILLUMINATING DEVICE

CROSS REFERENCE TO RELATED APPLICATION

This is a U.S. National Phase Application under 35 U.S.C. 371 of International Application PCT/JP2008/059805, filed May 28, 2008, which claims the priority of Japanese Application No. 2007-143049, filed May 30, 2007, the entire contents of both applications are hereby incorporated by reference.

TECHNICAL FIELD

The present invention relates to an electroluminescent element, a display device and an illuminating device employing the electroluminescent element.

TECHNICAL BACKGROUND

Electroluminescent displays are known as light emitting type electronic display device (ELD). An inorganic electroluminescent element and an organic electroluminescent element (organic EL element) are cited as the constituting element of the ELD. The inorganic EL element has been used as a planar light source, in which high alternative voltage is required for driving the light emitting device.

The organic EL element is an element having a light emitting layer placed between a cathode and an anode, in which electrons and positive holes are injected into the light emitting layer and excitons are generated by recombination of them, and fluorescence or phosphorescence light is emitted on the occasion of quenching of the excitons. Such device is noted because which can emit light by application of a voltage of several to several tens volts, and has wide viewing angle and high visibility since it is a self light emission type, and is completely solid state thin device suitable for space saving and portable appliance.

However, in an organic electroluminescence in view of the future practical application, desired has been development of an organic EL element which efficiently emits at a high luminance with a low electric consumption. In Japanese Patent No. 3093796, a slight amount of a fluorescent substance has been doped in a stilbene derivative, distyrylarylene derivative or a tristyrylarylene derivative, to achieve improved emission luminance and a prolonged lifetime of an element. Further, there are known such as an element having an organic emitting layer comprising a 8-hydroxyquinoline aluminum complex as a host compound which is doped with a slight amount of a fluorescent substance (for example, JP-A S63-264692) and an element having an organic emitting layer comprising a 8-hydroxyquinoline aluminum complex as a host compound which is doped with quinacridone type dye (for example, JP-A H03-255190).

In the case of utilizing emission from an excited singlet as described above, since a generation ratio of a singlet exciton to a triplet exciton is 1:3, that is, a generation probability of an emitting exciton species is 25% and a light taking out efficiency is approximately 20%, the limit of an external quantum efficiency ($\eta$ext) of taking out is said to be 5%.

However, since an organic EL element which utilizes phosphorescence from an excited triplet has been reported from Princeton University (M. A. Baldo et al., Nature vol. 395, pp. 151-154 (1998)), researches on materials exhibiting phosphorescence at room temperature have come to be active. For example, it is also disclosed in A. Baldo et al., Nature, vol. 403, No. 17, pp. 750-753 (2000), and U.S. Pat. No. 6,097,147.

It may be possible to realize about four times emission efficiency in principle by an organic EL element employing recently discovered phosphorescent emission in comparison with those employing conventional fluorescent emission. Development of the material therefore and further research and development of the layer arrangement and electrodes are conducted through the world. For example, in such as S. Lamansky et al., J. Am. Chem. Soc., vol. 123, p. 4304 (2001), many compounds mainly belonging to heavy metal complexes such as iridium complexes have been synthesized and studied.

Since the organic EL element is an all solid state element composed of a film of an organic material exhibiting about 0.1 µm in thickness in between two electrodes, and the light emission can be achieved with a relatively low voltage of 2 to 20 volts, the organic EL element is a promising technology for use as the next-generation flat display or lighting device.

It may be possible to realize about four times emission efficiency in principle by an organic EL element employing recently discovered phosphorescent emission in comparison with those employing conventional fluorescent emission. Development of the material therefore and further research and development of the layer arrangement and electrodes are conducted through the world.

The organic EL element is ought to be produced with low cost since it simply composed of an organic layer placed between a transparent electrode and a counter electrode and requires an extremely smaller number of parts than a liquid crystal display which is a representative plain display. However, the liquid crystal display actually leads in performance and cost.

One of a factor is a low productivity as for the cost. The almost of all the organic EL element is produced via so called vapor deposition method in which a layer is formed by a vapor deposition of a low molecular weight material. The vapor deposition method is very advantageous in efficiency and life time because an easily purified low molecular weight compound can be used for the organic EL element, a material with high purity can be easily obtained, and a multi-layered structure can be easily formed. Contrarily a layer forming apparatus is restricted since the deposition is conducted under a condition of high vacuum such as $10^{-4}$ Pa or less, and is disadvantageous in such low through-put that it is applicable to a substrate having small format and requires long time to form a plurality of layers. This is problematic in applied to an illumination use or a large format electric display, and this is one of the reason why the organic EL element is not practiced in these applications.

A coating method in which an organic layer is formed via spin coat, ink-jet, printing, spraying can form a layer having large area and is suitable for forming uniform layer having large area.

However, it is preferred plural functional layers are laminated to attain a high emission efficiency as well as ling life simultaneously. There is a method in which an upper layer is formed by coating employing a solvent which does not dissolve the lower layer when a low molecular weight compound is used to form plural layers by employing a coating method. However there is problem to deteriorate the element performance by breaking carrier balance due to generation of turbulence at the interface between layers when the upper layer is coated in the method described above.

Further, it is proposed that a high molecular weight compound is employed as for a material capable of coating. However it is difficult to apply because the high molecular weight compound is difficult to purify in general and a very few impurity causes deterioration of emission life time of the element in the organic EL element particularly.

There have been various technologies to dissolve the above-described problems. Examples include a technology where a constituting layer of an organic electroluminescent element is formed, and then the layer is polymerized, and in which technology bifunctional triphenylamine derivatives having two vinyl groups in their molecules are disclosed, and after the film formation of the compound, a three-dimensionally crosslinked polymer is formed (for example, refer to Patent Document 1); a technology where materials having two or more vinyl groups are incorporated into a plurality of layers, where the polymerization reaction is carried out via irradiation of the ultraviolet rays or heat at a step of forming an organic layer before an cathode is laminated (for example, refer to Patent Document 2); a production technology where a polymerization reaction is allowed to proceed during a film formation by adding an AIBN (azoisobutyronitrile), a radical generating agent, into a mixture of a material having vinyl groups at terminals of a phosphorescent light emitting dopant and a co-monomer similarly having vinyl groups (for example, refer to Patent Document 3); and a production technology where a Diels-Alder reaction is allowed to occur between two molecules within the same layer to result in a linkage (for example, refer to Patent Document 4).

However, there is no sufficient method to dissolve the problem of deterioration of the element due to turbulence between the interface in any technologies described above, and further, the influence of interface turbulence is remarkable in case that one of the layers to be laminated is an emitting layer.

Patent Document 1: JP-A H05-271166
Patent Document 2: JP-A 2001-297882
Patent Document 3: JP-A 2003-073666
Patent Document 4: JP-A 2003-086371

DISCLOSURE OF THE INVENTION

Problems to be Solved

An object of the present invention is to provide an organic EL element having high external quantum efficiency and long life, and an illumination device and a display device employing the organic EL element.

The above object of the present invention was achieved by the following embodiments.

1. An organic EL element comprising at least an anode and a cathode on a supporting substrate, and at least two layers of a first organic layer and a second organic layer between the anode and the cathode, wherein the first organic layer contains a light emitting dopant, the second organic layer contains an electron transport material and a part of material which composes the first organic layer, and the second organic layer is formed by a coating method after forming the first organic layer.
2. The organic EL element described in 1. above, wherein the second organic layer is formed on the first organic layer by a coating method.
3. The organic EL element described in 1. or 2. above, wherein the first organic layer is formed by a coating method.
4. The organic EL element described in any one of 1. through 3. above, wherein the organic EL element comprises three or more organic layers.
5. The organic EL element described in any one of 1. through 4. above, wherein the organic EL element comprises at least one of an anode buffer layer.
6. The organic EL element described in any one of 1. through 5. above, wherein the emitting dopant is a phosphorescent light emitting dopant.
7. The organic EL element described in 6. above, wherein the phosphorescent light emitting dopant is an iridium complex.
8. The organic EL element described in any one of 1. through 7. above, wherein the second organic layer contains an azacarbazole derivative.
9. The organic EL element described in any one of 1. through 8. above, wherein the first organic layer contains a compound represented by Formula (a).

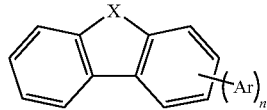

Formula (a)

In the formula (a) X is NR', O, S, CR'R" or SiR'R", wherein R' and R" is each a hydrogen atom or a substituent, Ar is an aromatic ring, n is an integer of 0 to 4.

10. The organic EL element described in 9. above, wherein the aromatic ring represented by Ar in Formula (a) is benzene ring or an aromatic heterocyclic ring in which 3 or more rings are condensed.
11. The organic EL element described in 9. or 10. above, wherein X is NR', O, or S in Formula (a).
12. The organic EL element described in any one of 1. through 11. above, wherein the first organic layer contains at least a compound having a reactive substituent or a polymer thereof.
13. The organic EL element described in any one of 1. through 12. above, wherein a part of material which composes the first organic layer contained in the first layer is a phosphorescent light emitting dopant.
14. The organic EL element described in any one of 1. through 13. above, which emits white light.
15. A display device providing an organic EL element described in any one of 1. through 14. above.
16. A illumination device providing an organic EL element described in any one of 1. through 14. above.

Advantage of the Invention

There have been provided an organic electroluminescent element exhibiting a high external quantum efficiency for taking out the light and having a prolonged emission life as well as a display device and a lighting device provided with the organic electroluminescent element based on the present invention.

DESCRIPTION OF SYMBOLS

Figure 1A:
FIG. 1 is a schematic drawing of a full color display device of an organic EL element.

101 glass substrate
102 ITO transparent electrode
103 dividing wall

104 positive hole injection layer
105B, 105G, 105R emitting layer Optimal Embodiment of the Invention The present invention is detailed.

The present invention is featured by that in an organic EL element comprising at least an anode and a cathode on a supporting substrate, and at least two layers of a first organic layer and a second organic layer between the anode and the cathode, wherein the first organic layer contains a light emitting dopant, the second organic layer contains an electron transport material and a part of material which composes the first organic layer, and the second organic layer is formed by a coating method after forming the first organic layer.

The inventors have found that carrier balance is improved and element performance is enhanced by a result of ejecting carrier efficiently between the emitting layer and organic layer by incorporating a part of the material which composes the first organic layer into the second organic layer in a process of laminating the second organic layer on the first organic layer by coating, and completed the invention. Another layer may exist between the first organic layer and the second organic layer.

The term "a part of the material which composes the first organic layer" may be, in case that the first organic layer contains plural low molecular weight compounds, one of the low molecular weight compounds, and, in case that the first organic layer contains a polymer or an oligomer, a low molecular weight molecule comprising a structure of their recurring units.

It may be possible that the part of the material composing the first organic layer is incorporated in the second organic layer by the second organic layer is formed on the first organic layer by employing a coating composition to form the second organic layer whereby a part of the material composing the first organic layer elutes into the second organic layer.

<<Layer Arrangement of Organic EL Element and Organic Layer>>

Structural layer of the organic EL element of the invention is described. Preferable concrete examples of the layer constitution of the organic EL element of the invention are listed below, though the invention is not limited to them.

(1) Anode/Light emitting layer/Electron transport layer/Cathode (2) Anode/Positive hole transport layer/Light emitting layer/Electron transport layer/Cathode (3) Anode/Positive hole transport layer/Light emitting layer/Positive hole blocking layer/Electron transport layer/Cathode (4) Anode/Positive hole transport layer/Light emitting layer/Positive hole blocking layer/Electron transport layer/Cathode buffer layer/Cathode (5) Anode/Anode buffer layer/Positive hole transport layer/Light emitting layer/Positive hole blocking layer/Electron transport layer/Cathode buffer layer/Cathode <<Organic Layer>>

The organic layer of this invention is described.

The organic EL element of this invention preferably comprises plural organic layers as composing layers, wherein the organic layers include a positive hole transport layer, a light emitting layer, a positive hole blocking layer and an electron transport layer among those listed above, and further include a composition layer of the organic EL element such as positive hole injection layer, an electron injection layer when it contains an organic compound.

Further an anode buffer layer, a cathode buffer layer and so on composes the organic layer when an organic compound is employed in these layers.

A compound employed in the second organic layer according to this invention includes a pyridine derivative, an azacarbazole derivative and so on, and the azacarbazole derivative is preferable. The azacarbazole is a compound shown by the following formula (B) wherein one or more carbon atoms represented by $X_1$ through $X_8$ is substituted by a nitrogen atom.

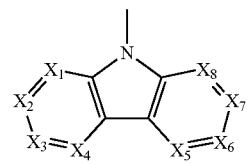

Formula (B)

Practical examples of compounds employed in the second organic layer, which is not limitative.

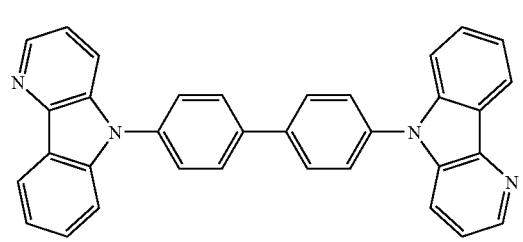

C-1

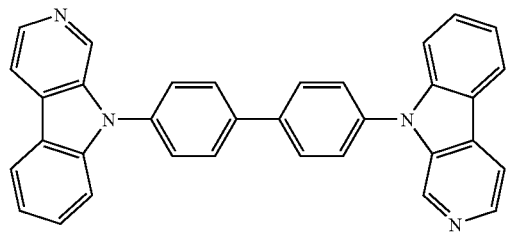

C-2

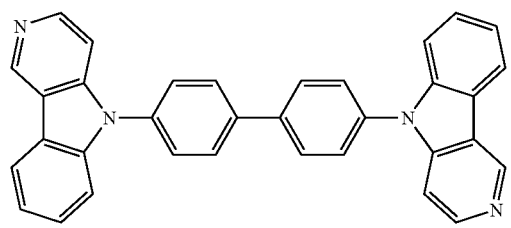

C-3

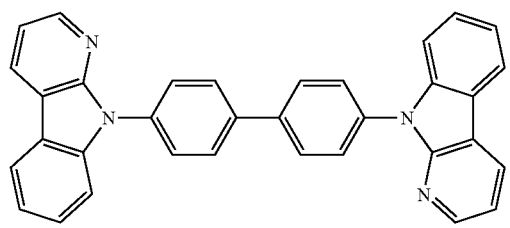

C-4

-continued
C-5
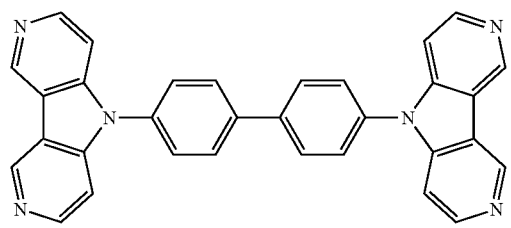
C-6
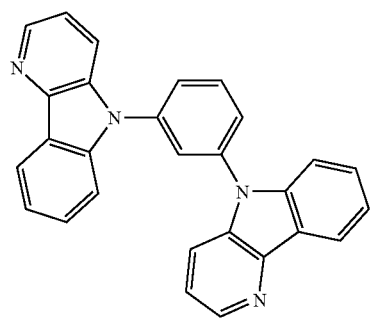
C-7
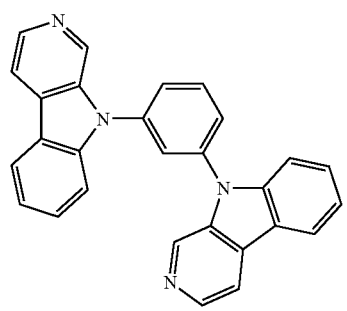
C-8
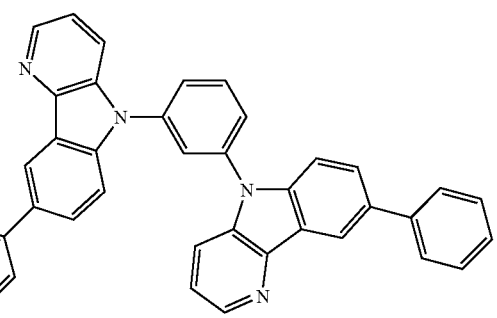
C-9
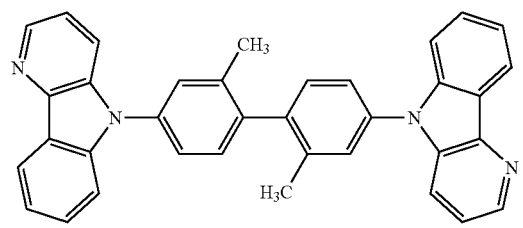
C-10
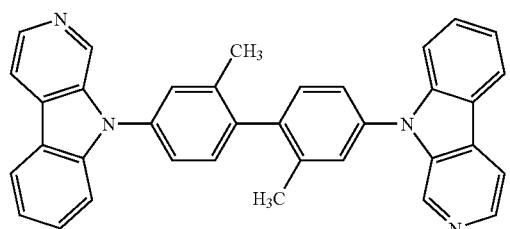
C-11
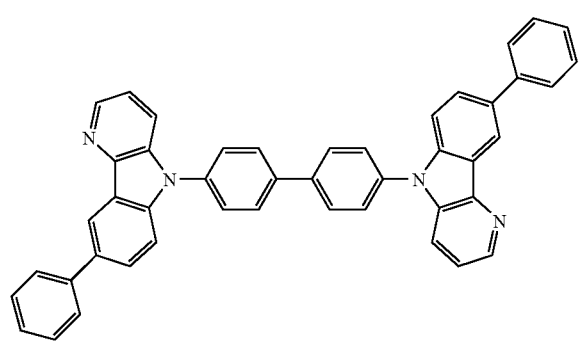
C-12
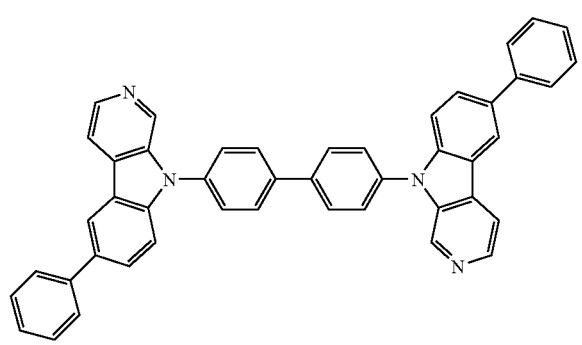
C-13
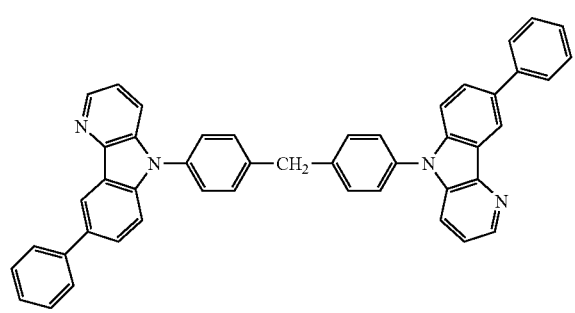
C-14
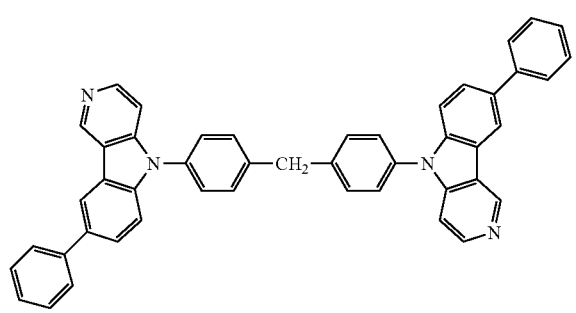

-continued
C-15
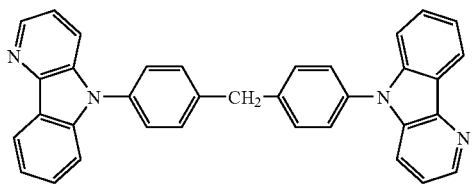
C-16
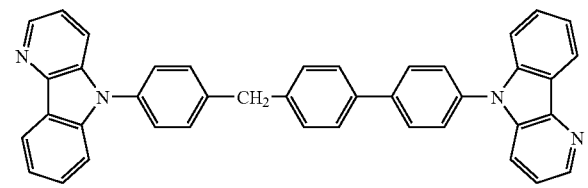
C-17
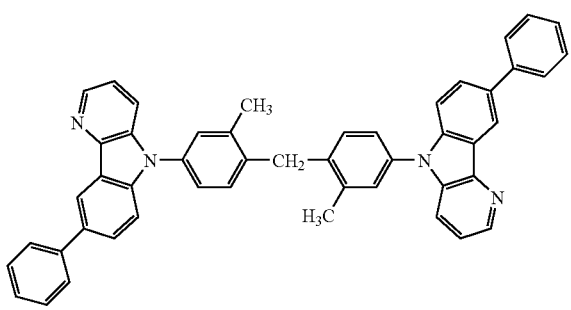
C-18
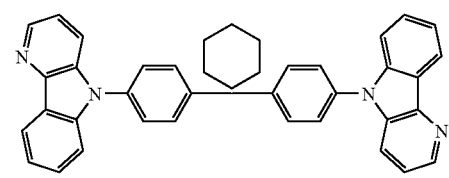
C-19
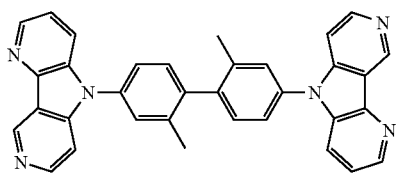
C-20
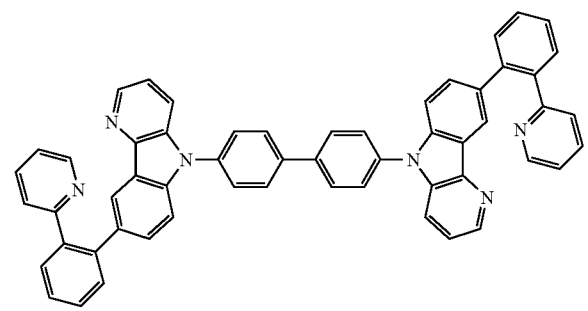
C-21
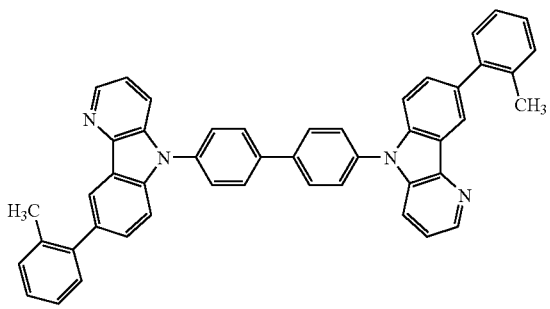
C-22
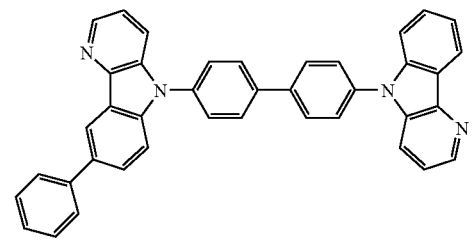
C-23
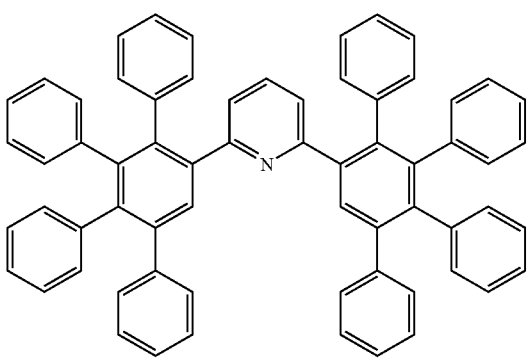
C-24
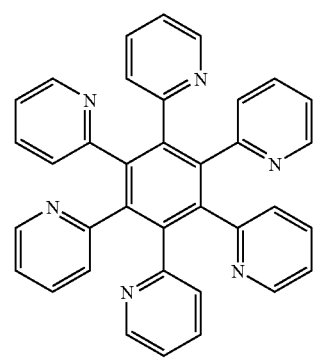

-continued
C-25
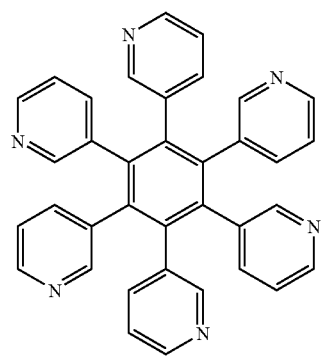
C-26
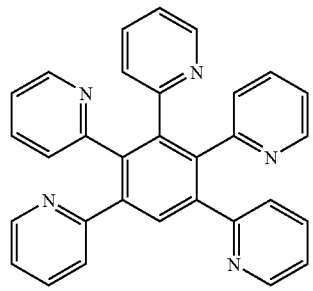
C-27
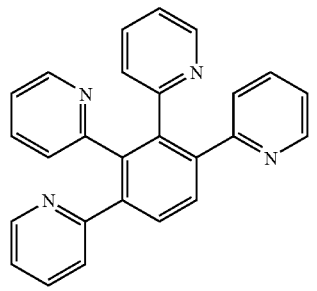
C-28
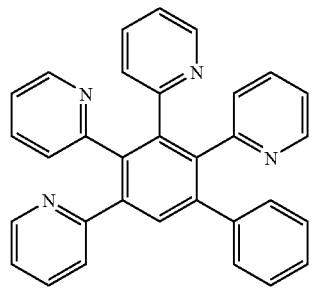
C-29
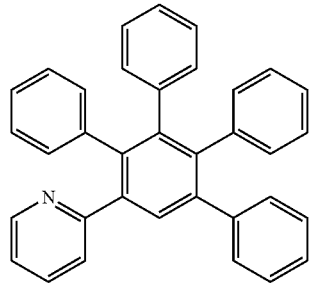
C-30
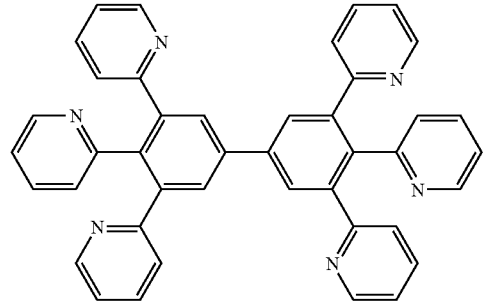
C-31
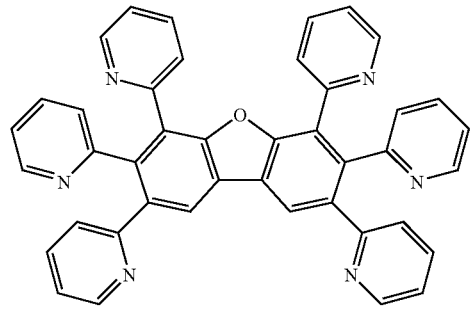
C-32
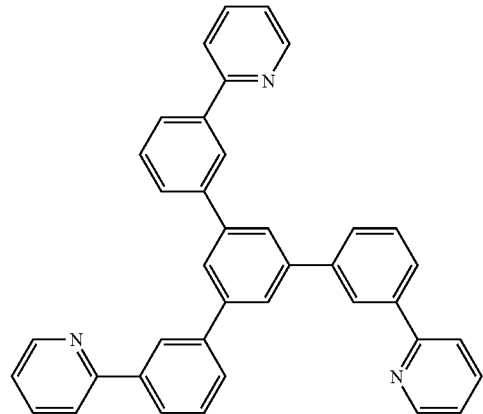

-continued
C-33
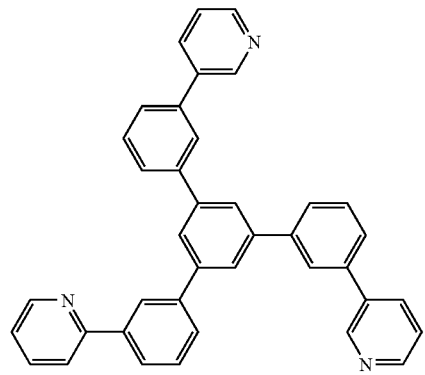
C-34
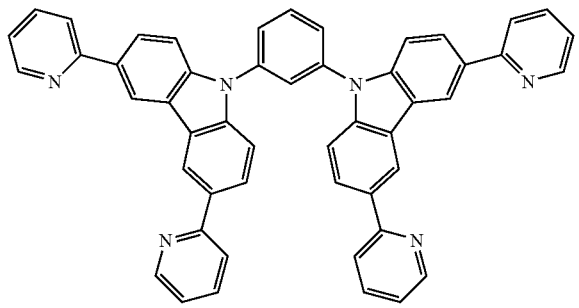
C-35
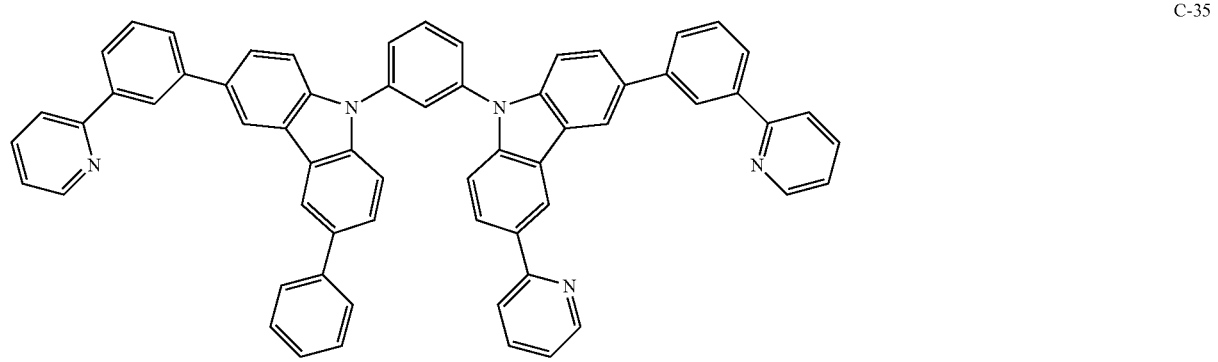
C-36
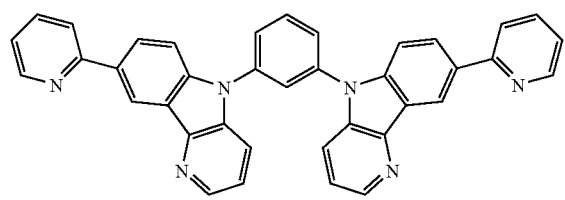
C-37
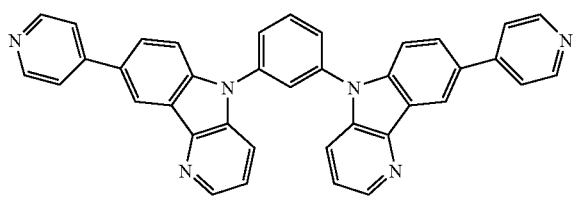
C-38
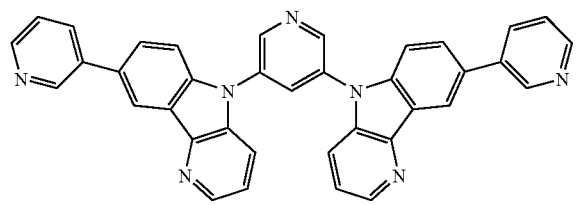
C-39
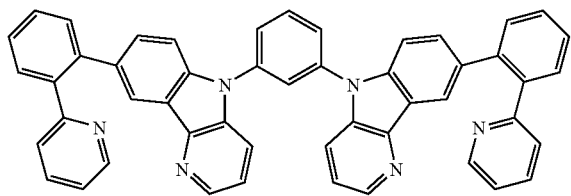
C-40
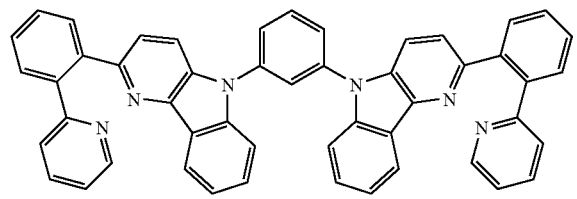
C-40
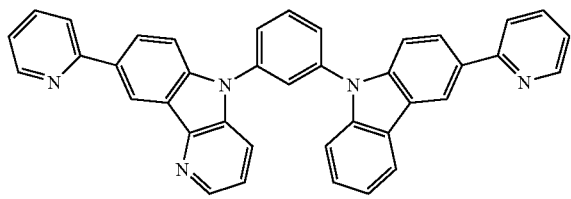

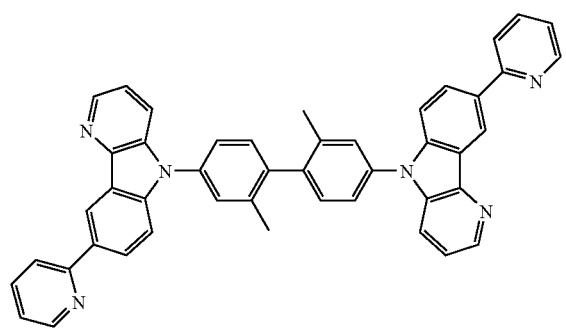

C-42

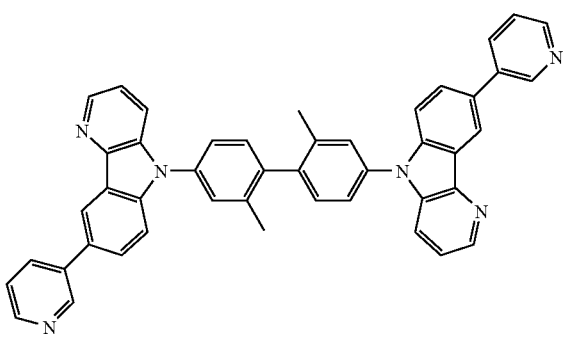

C-43

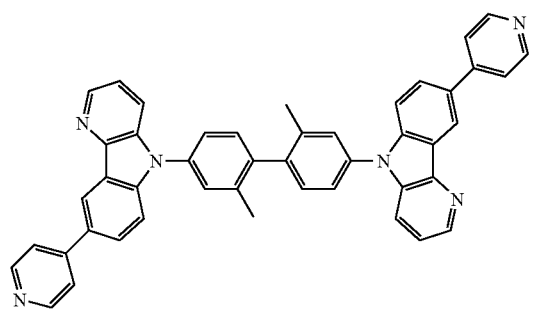

C-44

C-45

The maximum wave length of the emission of the blue emitting layer is preferably 430 to 480 nm, the maximum wave length of the emission of the green emitting layer is preferably 600 to 640 nm, and maximum wave length of the emission of the red emitting layer is preferably 430 to 480 nm in the organic EL element of this invention. The display apparatus preferably employs this organic EL element. A white emitting layer may be composed by superposing at least these three emitting layers. The organic EL element may comprise a non-emission intermediate layer between the emitting layers. The organic EL element is preferably a white emitting layer, and a display element employing this.

Layers composing the organic EL element of this invention will be described.

<<Light Emitting Layer>>

The light emitting layer relating to the invention is a layer in which electrons and positive holes each injected from the electrodes or the electron transport layer and the positive hole transport layer, respectively, are recombined to emit light and the portion of light emission may be inside of the layer or the interface of the light emitting layer and the adjacent layer.

The total thickness of the light emitting layer is not specifically restricted but preferably within the range of from 2 nm to 5 μm, more preferably from 2 nm to 200 nm, and particularly preferably from 10 nm to 20 nm in view of uniformity of the layer, preventing the application of unnecessary high voltage at the light emission and improving stability of emission color against driving current.

The light emitting layer can be prepared by forming a layer of the later-mentioned light emitting dopant and the host compound by known method such as a vacuum deposition method, spin coating method, LB method and ink-jet method.

The emitting layer of the organic EL element of this invention preferably contains an emitting compound and at least one of light emitting dopant, that is, a phosphorescent dopant (a phosphorescent light emitting dopant) or a fluorescent dopant (a fluorescent light emitting dopant) Host Compound (Emission Host)

The host compound used in this invention will be described.

As the host compound to be contained in the light emitting layer of the organic EL element, a compound is defined as a compound having a weight ratio of the host compound in the compounds contained in the light emitting layer is not less than 20%, and having a phosphorescent quantum efficiency of the fluorescent light emission of less than 0.1 and more preferably less than 0.01 at room temperature (25° C.). The weight ratio of the host compound in the compounds contained in the light emitting layer is preferably not less than 20%.

As the host compound, known host compounds may be used singly or in a combination of plural kinds thereof. The transport of charge can be controlled by the combination use of the host compounds so as to raise the efficiency of the organic EL element. Moreover, mixing of different emitted light is made possible by the use of plural kinds of light emitting material so as that optional color light can be obtained.

As the host compound, a compound is preferable which has positive hole transport ability and electron transport ability, an ability to prevent shift of emitted light to loner wavelength side and high glass transition point Tg.

A host compound employed in the first organic layer includes the compound represented by formula (a) described above.

In the formula (a) X is NR', O, S, CR'R" or SiR'R", wherein R' and R" is each a hydrogen atom or a substituent. Ar is an aromatic ring, n is an integer of 0 to 4. The compound represented by formula (a) may have a substituent other than Ar.

In Formula (a), the substituents represented by each of R' and R" in X include an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, or a pentadecyl group); a cycloalkyl group (for example, a cyclopentyl group or a cyclohexyl group); an alkenyl group (for example, a vinyl group, an allyl group, a 1-propenyl group, a 2-butenyl group, a 1,3-butadienyl group, a 2-pentenyl group, or an isopropenyl group); an alkynyl group (for example, an ethynyl group or a propargyl group); an aromatic hydrocarbon group (also referred to as an aromatic carbon ring group or an aryl group, for example, a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, and a biphenylyl group); an aromatic heterocyclyl group (for example, a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, a carbazolyl group, a carbolinyl group, and a diazacarbazolyl group (referring to the group in which any one of carbon atoms constituting the carboline ring of the aforesaid carbolinyl group is replaced with a nitrogen atom), and a phthalazinyl group); a heterocyclyl group (for example, a pyrrolidyl group, an imidazolyl group, a morpholyl group, and an oxazolidyl group); an alkoxy group (for example, a methoxy group, an ethoxy group, a propyloxy group, a pentyloxy group, a hexyloxy group, an octyloxy group, and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, a hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group, a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-pyridylaminoureido group); a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsulfinyl group); an alkylsulfonyl group (for example, a methylsulfonyl group, an ethylsulfonyl group, a butylsulfonyl group, a cyclohexylsulfonyl group, a 2-ethylhexylsulfonyl group, and a dodecylsulfonyl group); an arylsulfonyl or heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a 2-ethylhexylamino group, a dodecylamino group, an anilino group, a naphthylamino group, and a 2-pyridylamino group); a halogen atom (for example, a fluorine atom, a chlorine atom, and a bromine atom); a fluorinated hydrocarbon group (for example, a fluoromethyl group, a trifluoromethyl group, a pentafluoroethyl group, and a pentafluorophenyl group); a cyano group, a nitro group, a hydroxyl group, a mercapto group; a silyl group (for example, a trimethylsilyl group, a triisopropylsilyl group, a triphenylsilyl group, and a phenyldiethylsilyl group); and a phosphono group.

These substituents may be further substituted with the aforesaid substituents. Further, a plurality of these substituents may be combined with each other to form a ring.

Preferable example of X in the formula (a) is NR' or O, and an aromatic hydrocarbon group and an aromatic heterocyclic group are most preferable for R'.

Examples of the aromatic group represented by Ar include an aromatic hydrocarbon group and an aromatic heterocyclic group. The aromatic ring may be a single ring or condensed ring, and may have no substituent or a substituent mentioned later.

Examples of the aromatic hydrocarbon ring represented by Ar in the formula (a) include a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, an m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring and an anthranthrene ring. These aromatic heterocyclic rings or aromatic hydrocarbon rings may have a substituent.

In Formula (a), examples of an aromatic heterocycle represented by Ar are as follows: a furan ring, a dibenzofuran ring, a thiophene ring, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, an indazole ring, a benzimidazole ring, a benzothiazole ring, a benzooxazole ring, a quinoxaline ring, a quinazoline ring, a cinnoline ring, a quinoline ring, an isoquinoline ring, a phthalazine ring, naphthyridine ring, a carbazole ring, a carboline ring, a diazacarbazole ring (indicating a group in which one of the carbon atoms constituting the carboline ring is replaced with a nitrogen atom). These rings may further have a substituent.

Among these rings, preferably used as an aromatic ring represented by Ar in Formula (a) are: a carbazole ring, a carboline ring, a dibenzofuran ring, and benzene ring. Especially preferable rings are: a carbazole ring, a carboline ring, and benzene ring. Among these, a benzene ring having a substituent is more preferable, and in particular, a benzene ring having a carbazolyl group is most preferable.

In one of a preferable embodiment an aromatic ring represented by Ar in the Formula (a), are condensed rings with three or more rings, and specific examples of a condensed aromatic hydrocarbon ring having three or more rings are:

a naphthacene ring, an anthracene ring, a tetracene ring, a pentacene ring, a hexacene ring, a phenanthrene ring, a pyrene ring, a benzopyrene ring, a benzazulene ring, a chrysene ring, a benzochrysene ring, an acenaphthene ring, an acenaphthylene ring, a triphenylene ring, a coronene ring, a benzocoronene ring, a hexabenzocorone ring, a fluorene ring, a benzofluorene ring, a fluoranthene ring, a perylene ring, a naphthoperylene ring, a pentabenzoperylene ring, a benzoperylene ring, a pentaphene ring, a picene ring, a pyranthrene ring, a coronene ring, a naphthacoronene ring, an ovalene ring, an anthraanthrene ring. In addition, these rings may further have a substituent.

Moreover, examples of a condensed aromatic heterocycle having three or more rings are: an acridine ring, a benzoquinoline ring, a carbazole ring, a carboline ring, a phenazine ring, a phenanthridine ring, a phenanthroline ring, a carboline ring, a cycladine ring, a quindoline ring, a thebenidine ring, a quinindoline ring, a triphenodithiazine ring, a triphenodioxazine ring, a phenanthrazine ring, an anthrazine ring, a perimizine ring, a diazacarbazole ring (indicating a ring structure in which one of the carbon atoms constituting the carboline ring is replaced with a nitrogen atom), a phenanthroline ring, a dibenzofuran ring, a dibenzothiophene ring, a naphthofuran ring, a naphthothiophene ring, a benzodifuran ring, a benzodithiophene ring, a naphthodifuran ring, a naphthodithiophene ring, an anthrafuran ring, an anthradifuran ring, an anthrathiophene ring, an anthradithiophene ring, a thianthrene ring, a phenoxthine ring, and a thiophanthrene ring (naphthothiophene ring). These rings may further have a substituent.

Here, in Formula (a), the substituents which an aromatic ring represented by Ar may have are synonymous with the substituents represented by R' or R".

Moreover, in Formula (a), although n represents an integer of 0 to 4, n is preferably an integer of 0 to 2. Especially, when X is O or S, it is preferable that n is 1 or 2. Ar may be same or different when n is 2 or more.

Examples of a luminescence host compound represented by Formula (a) are shown below, however, the present invention is not limited to these:

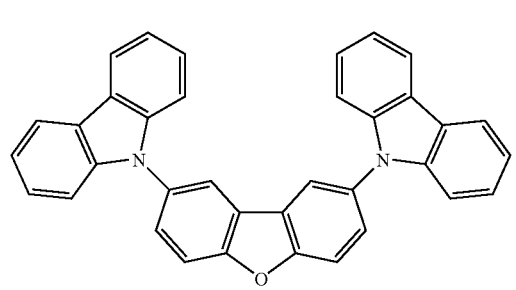

a-1

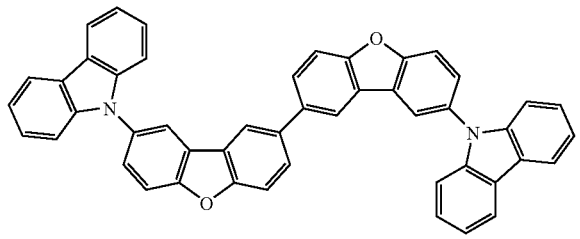

a-2

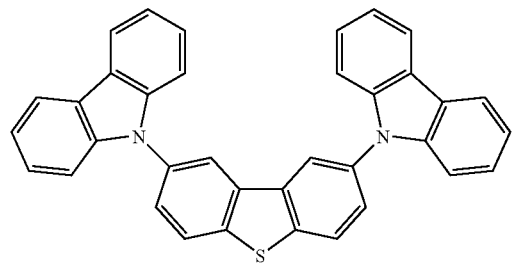

a-3

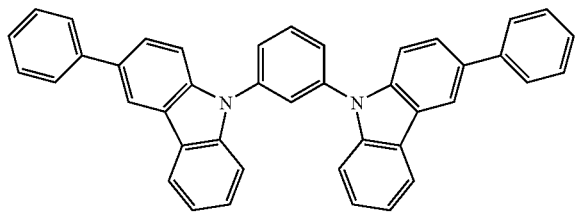

a-4

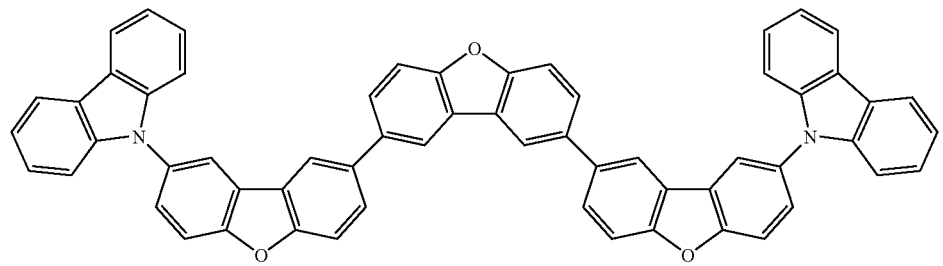

a-5

-continued
a-6
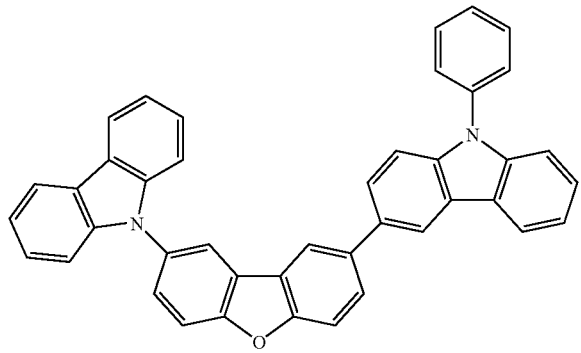
a-7
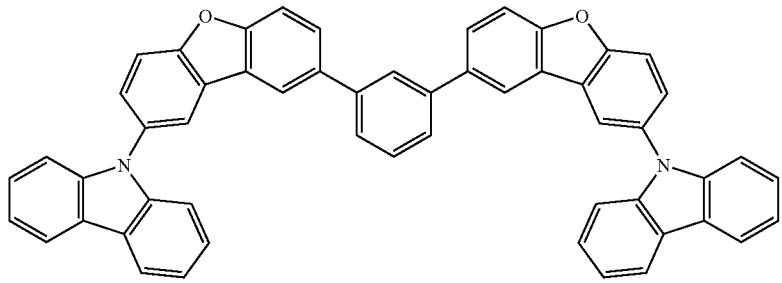
a-8
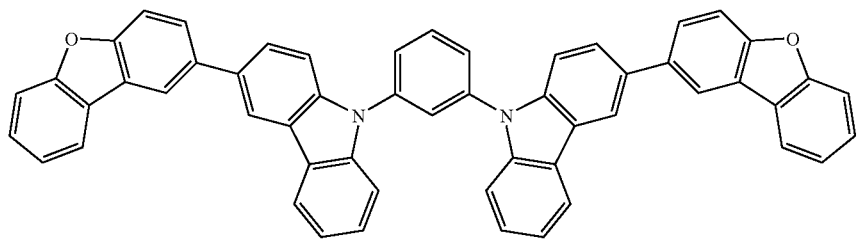
a-9
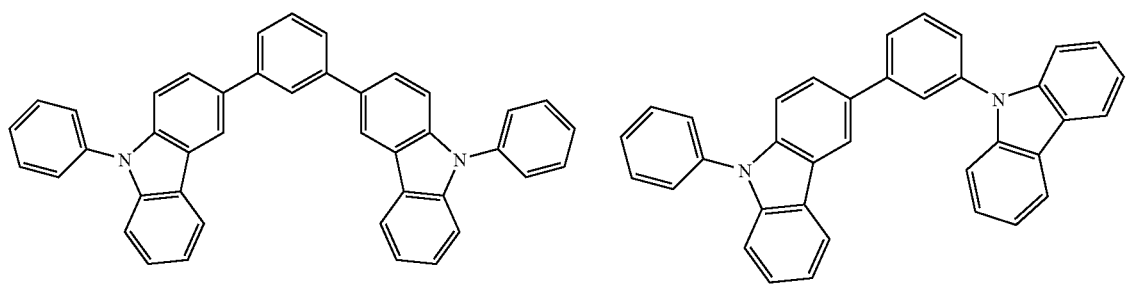
a-10
a-11
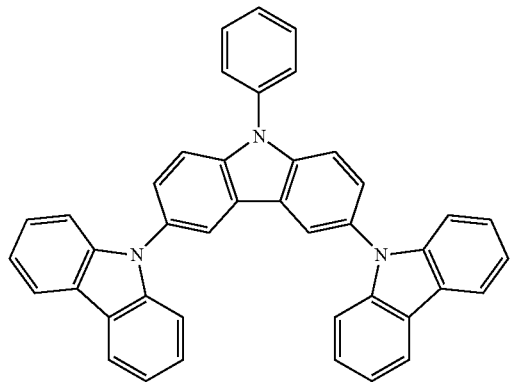
a-12
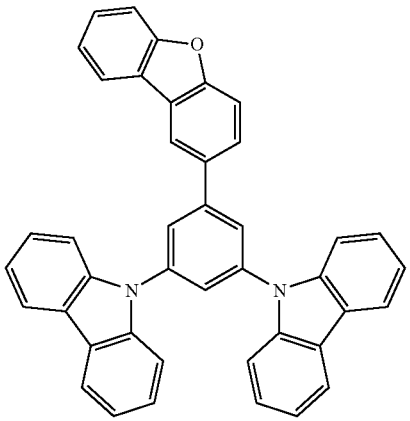

-continued
a-13
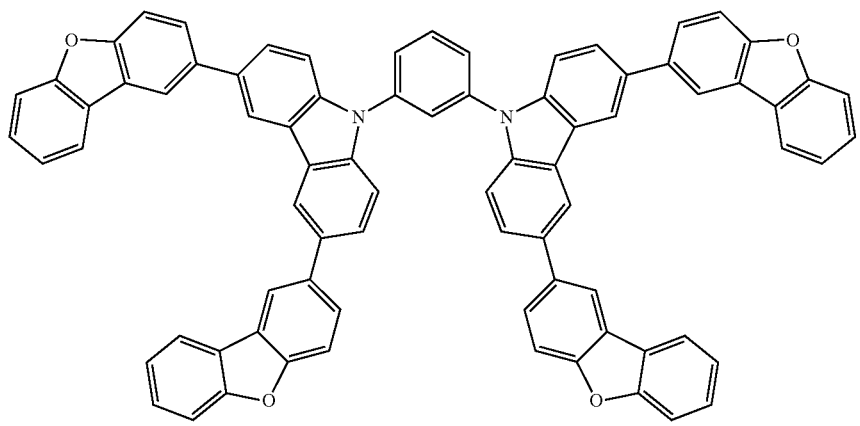
a-14
a-15
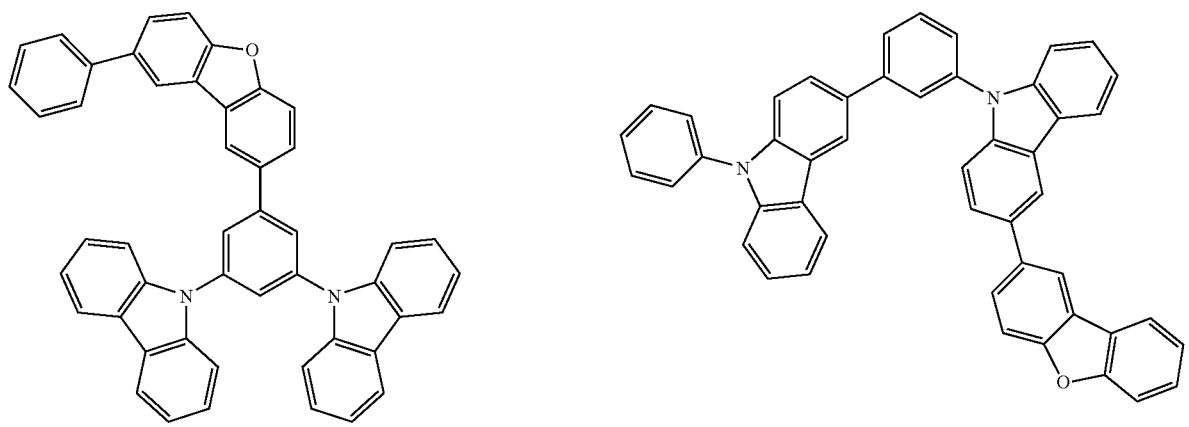
a-16
a-17
a-18
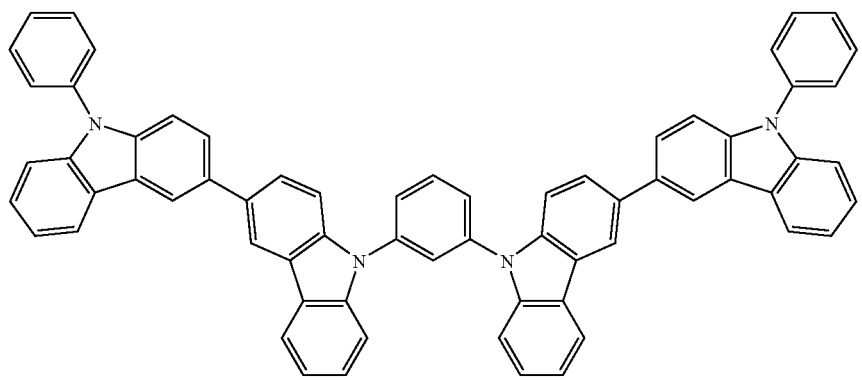
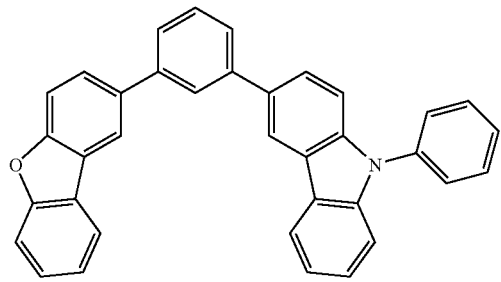
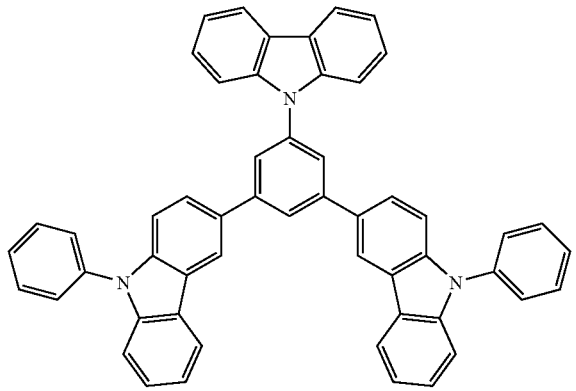

-continued
a-19
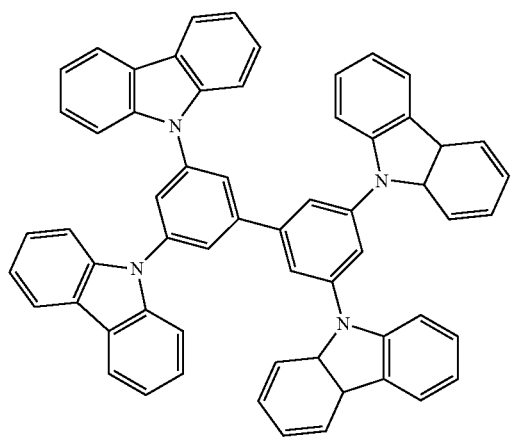
a-20
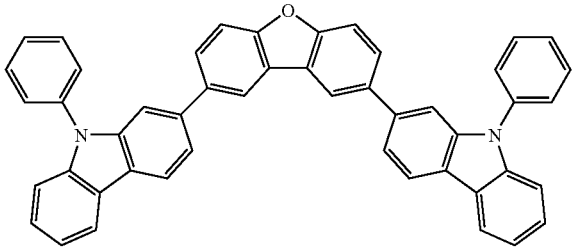
a-21
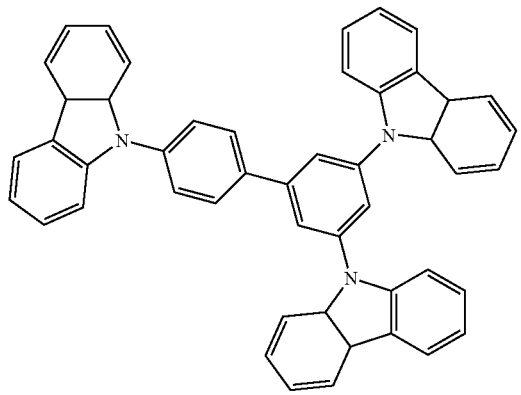
a-22
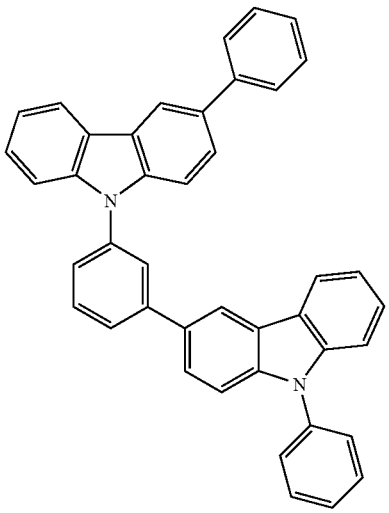
a-23
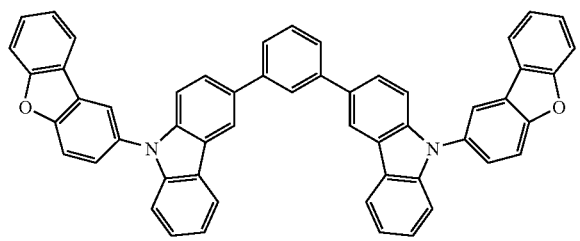
a-24
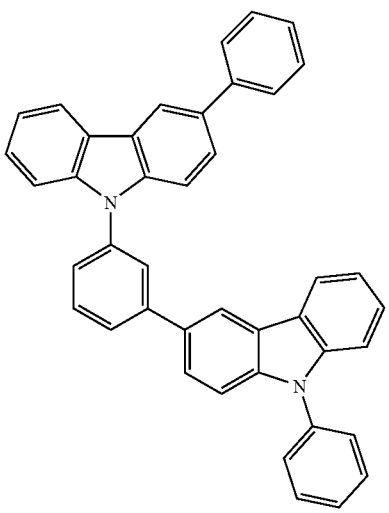

-continued
a-25
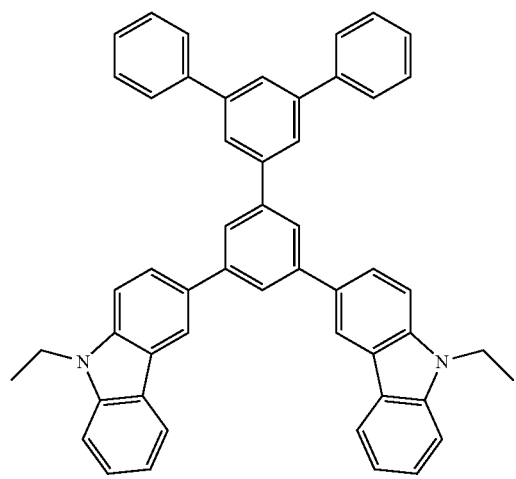
a-26
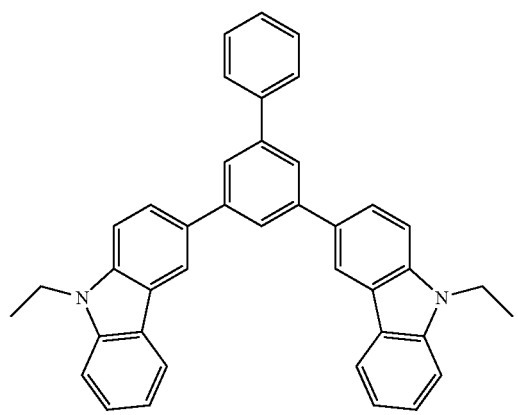
a-27
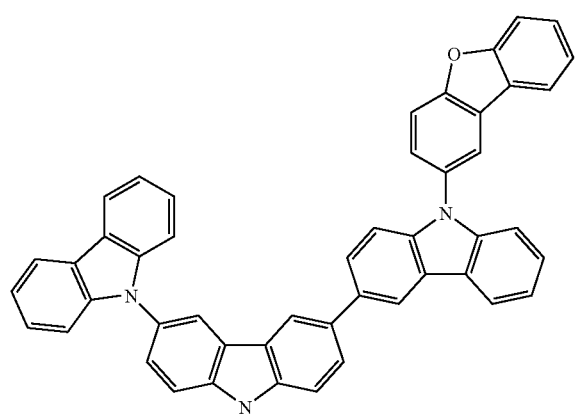
a-28
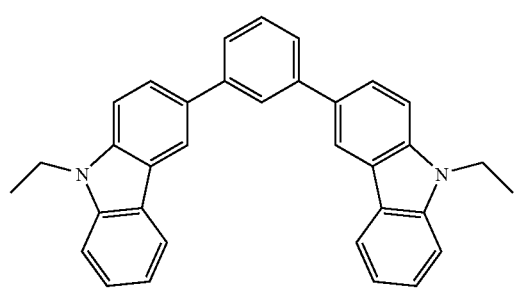
a-29
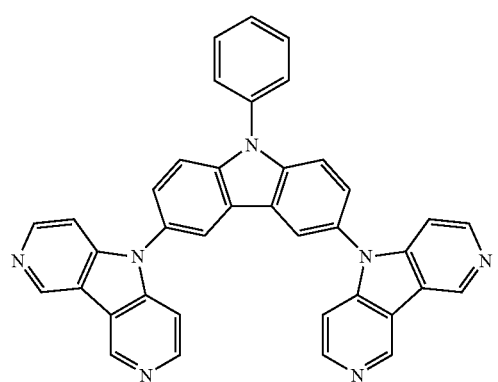
a-30
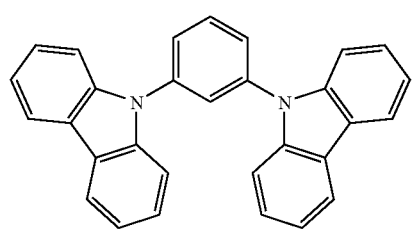

-continued
a-31
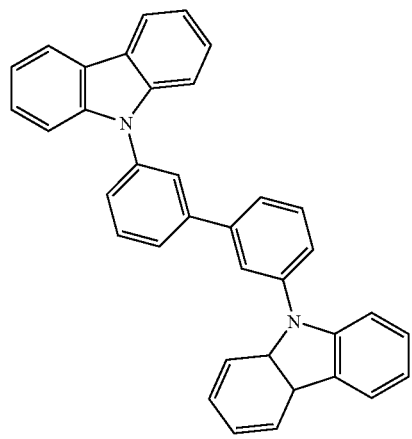
a-32
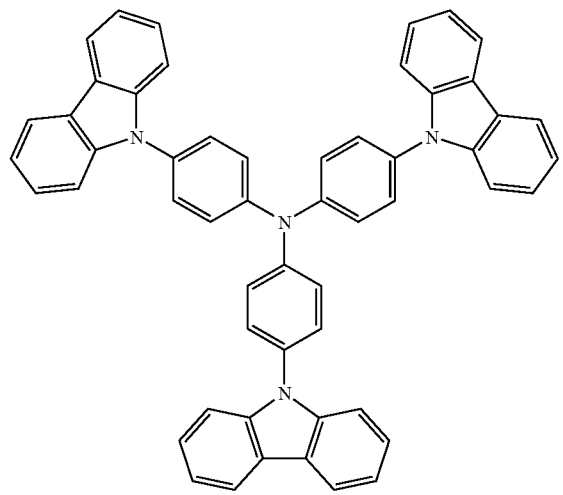
a-33
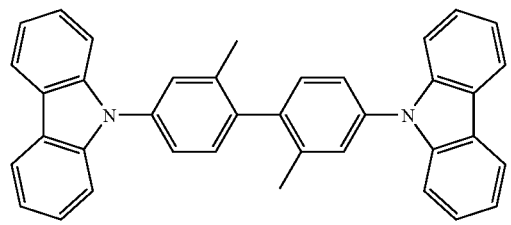
a-34
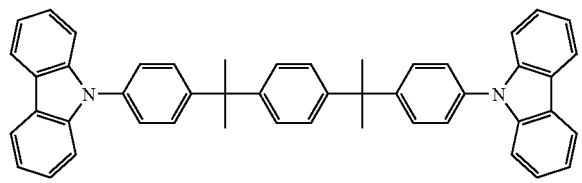
a-35
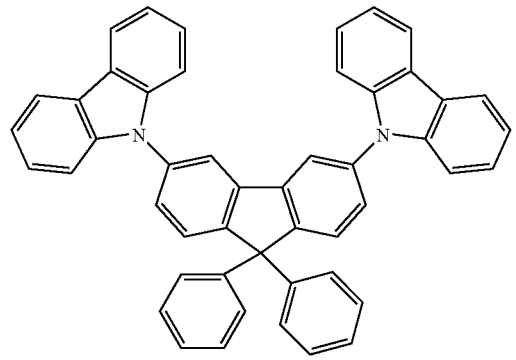
a-36
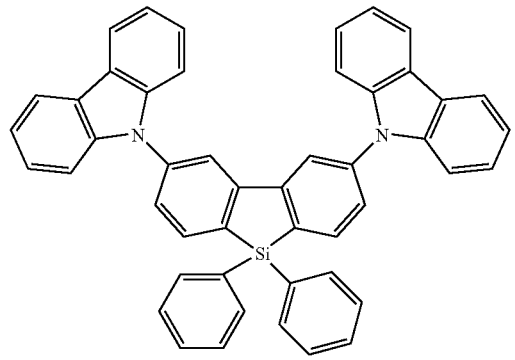
a-37
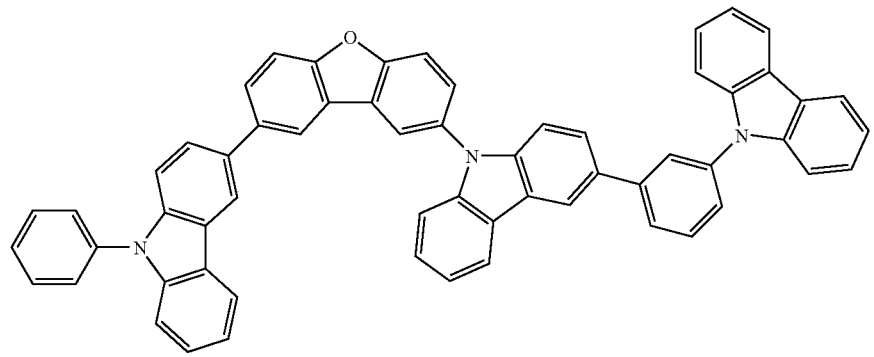

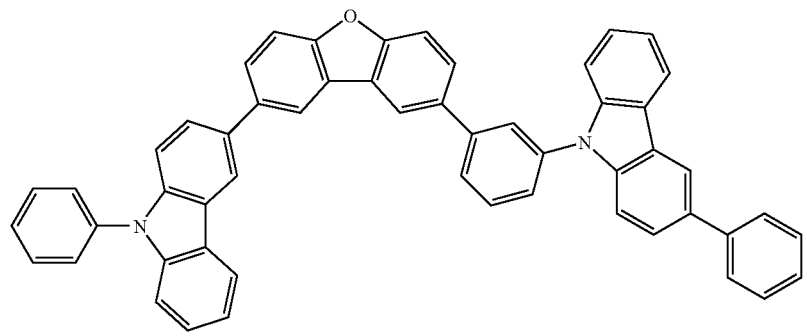
a-38
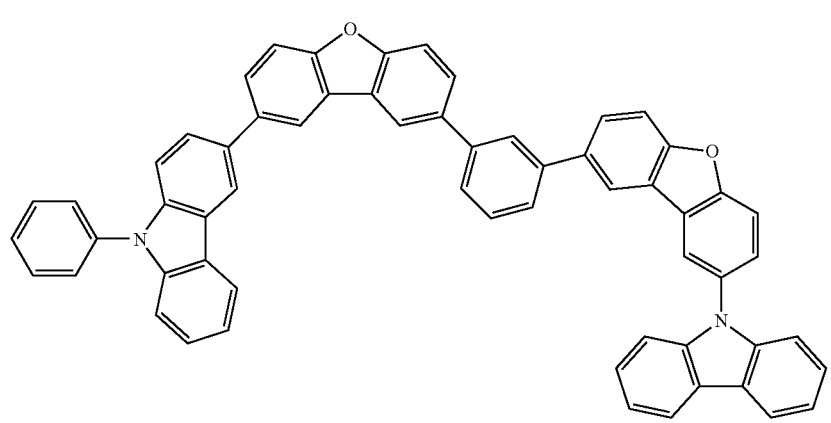
a-39
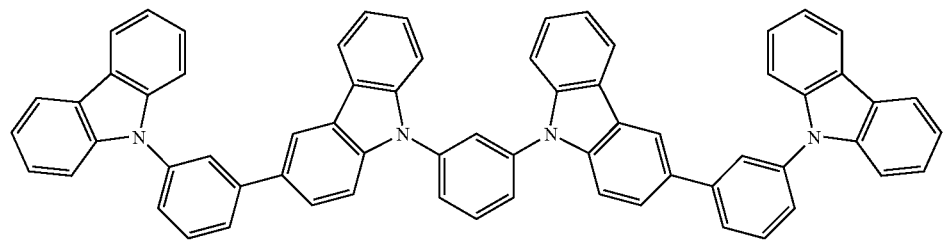
a-40
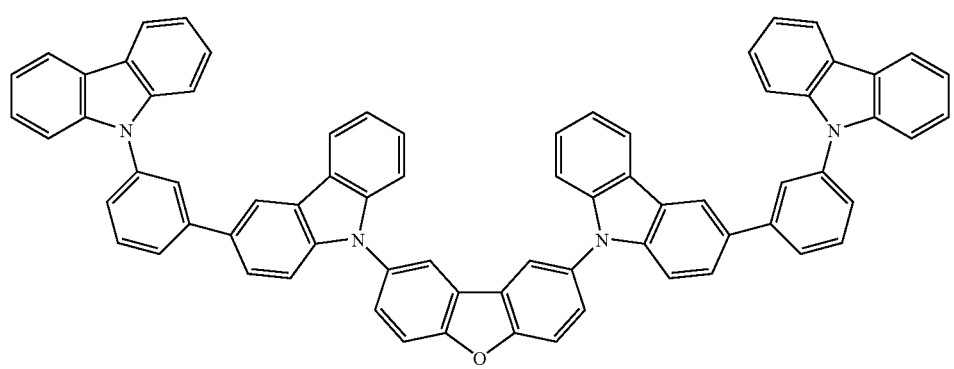
a-41 a-42
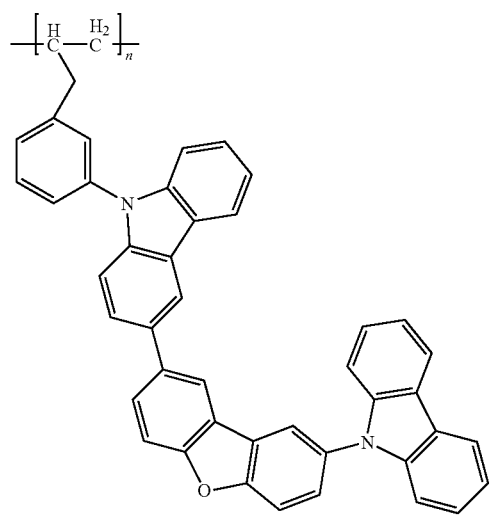

a-43
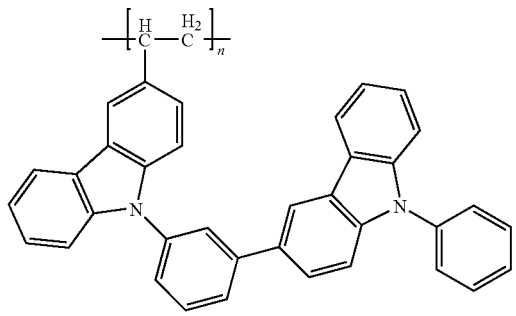

As examples of a known emission host, compounds described in the following Documents are preferable:

For example, JP-A 2001-257076, JP-A 2002-308855, JP-A 2001-313179, JP-A 2002-319491, JP-A 2001-357977, JP-A 2002-334786, JP-A 2002-8860, JP-A 2002-334787, JP-A 2002-15871, JP-A 2002-334788, JP-A 2002-43056, JP-A 2002-334789, JP-A 2002-75645, JP-A 2002-338579, JP-A 2002-105445, JP-A 2002-343568, JP-A 2002-141173, JP-A 2002-352957, JP-A 2002-203683, JP-A 2002-363227, JP-A 2002-231453, JP-A 2003-3165, JP-A 2002-234888, JP-A 2003-27048, JP-A 2002-255934, JP-A 2002-260861, JP-A 2002-280183, JP-A 2002-299060, JP-A 2002-302516, JP-A 2002-305083, JP-A 2002-305084 and JP-A 2002-308837.

The emission host employed in this invention preferably contains at least one of a compound having a reactive substituent or its polymer.

The reactive substituent includes a substituent containing a carbon-carbon double bond, preferably a vinyl group. It is preferred that the compound having a reactive substituent has two or more reactive substituents.

Examples of compound having a reactive substituent or its polymer are listed below.

1-1
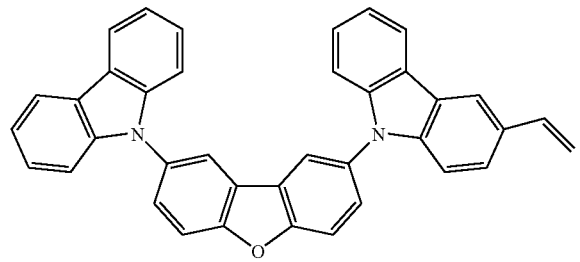

1-2
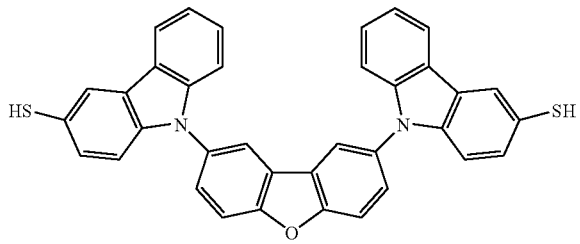

1-3
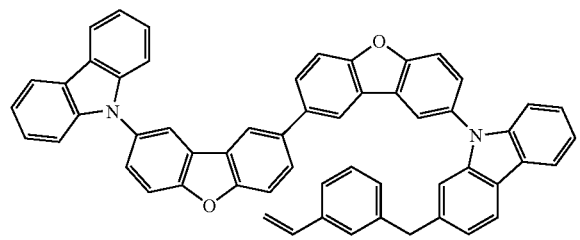

1-4
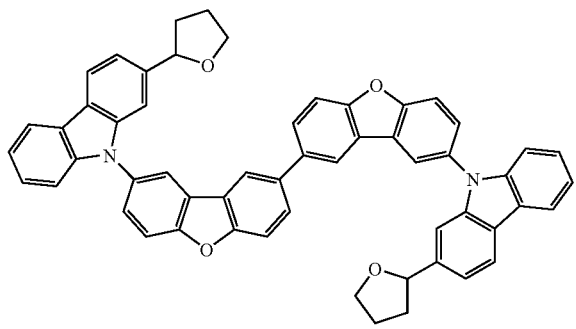

-continued
1-5
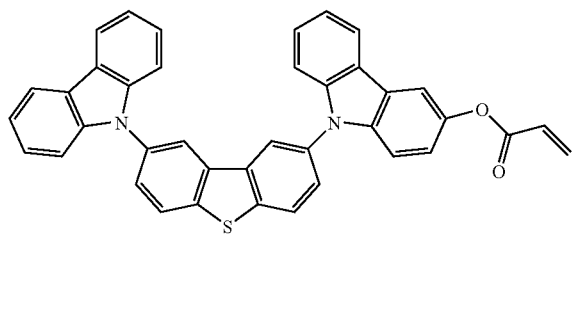
1-6
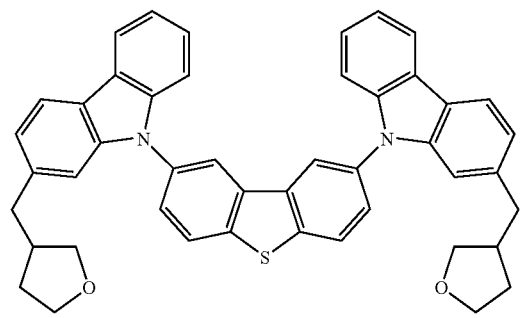
1-7
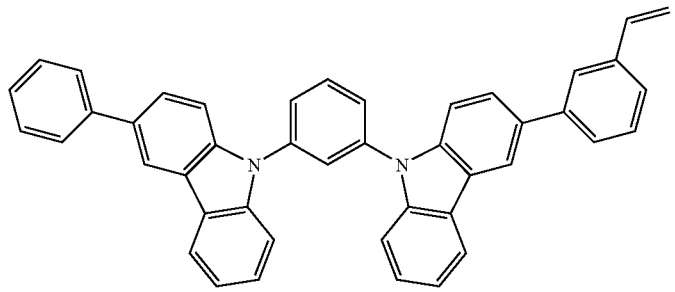
1-8
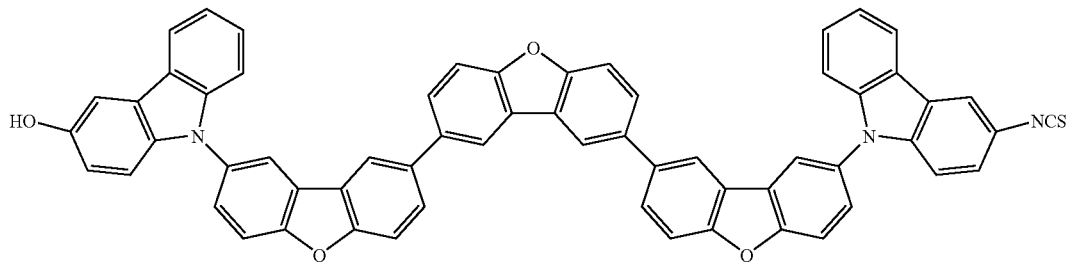
1-9
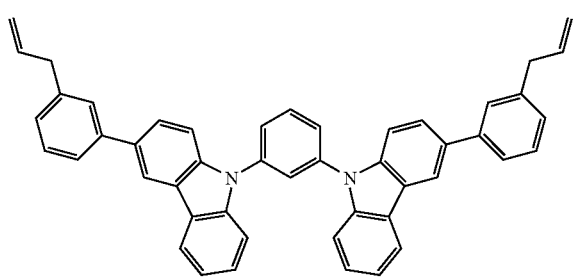
1-10
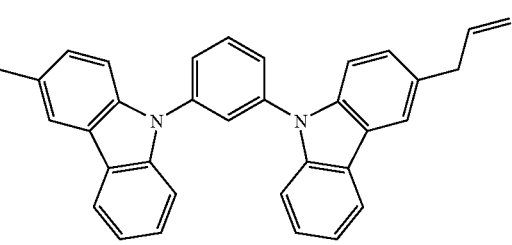
1-11
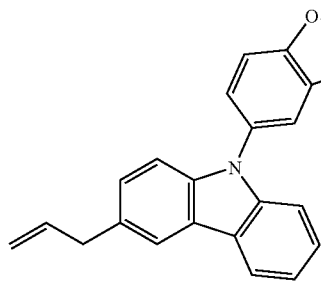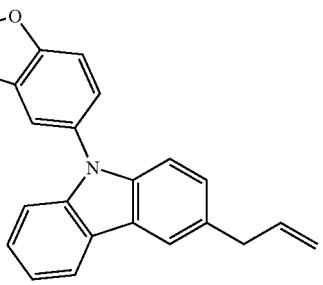

-continued
1-12
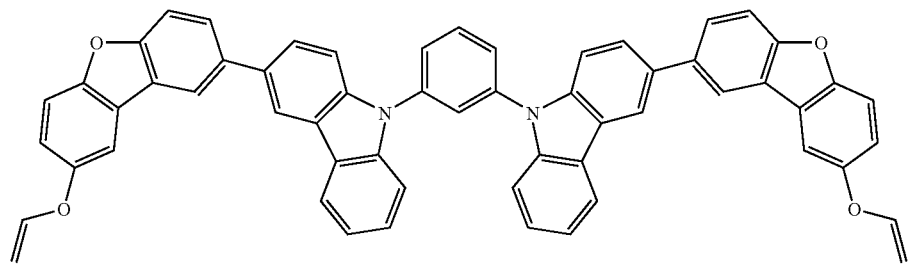
1-13
1-14
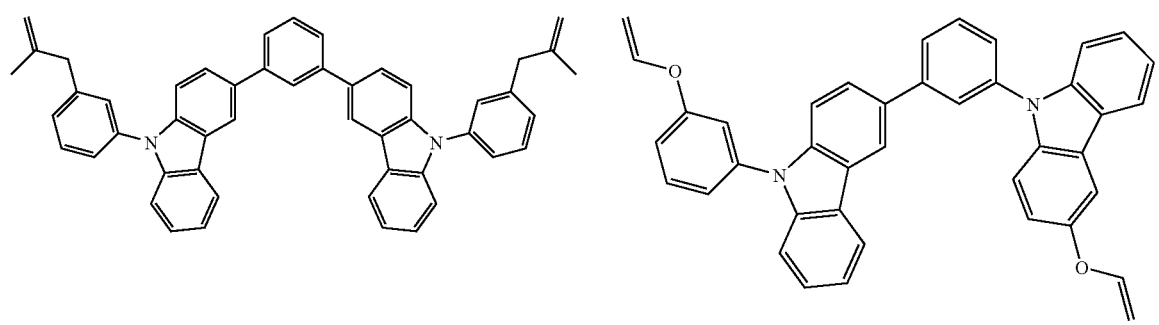
1-15
1-16
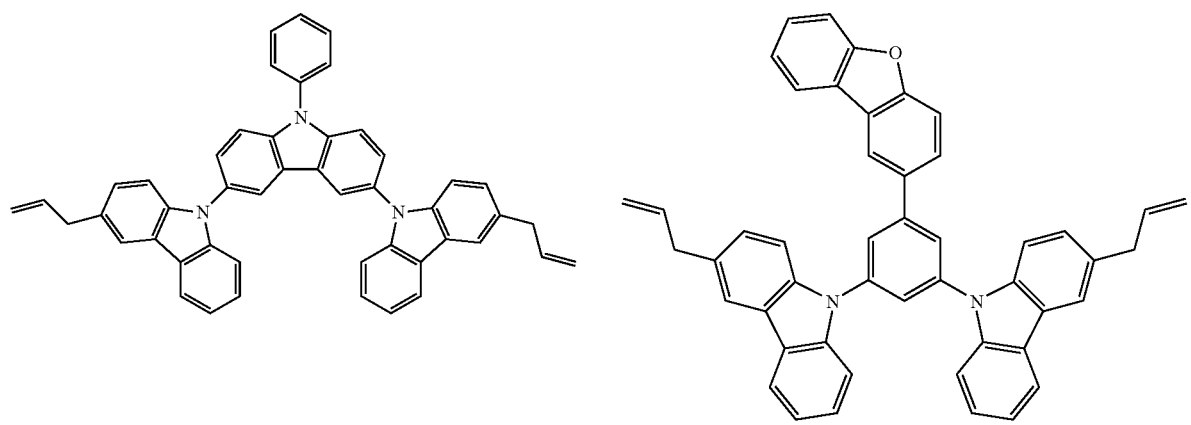
1-17
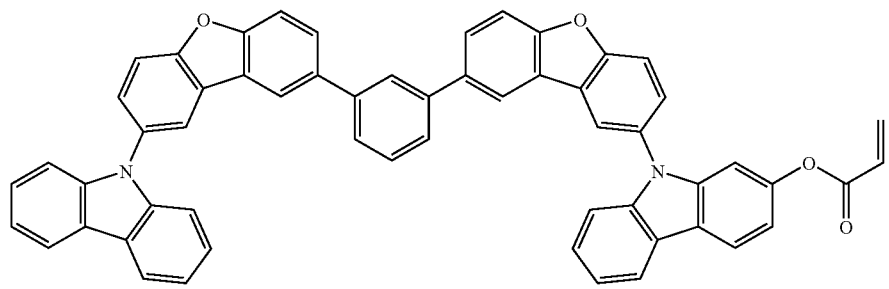
1-18
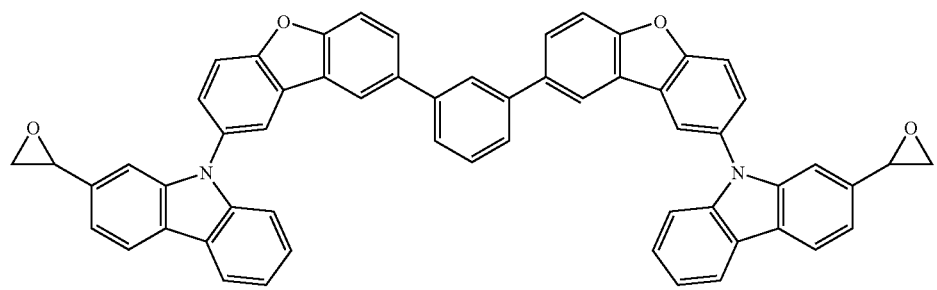

1-19
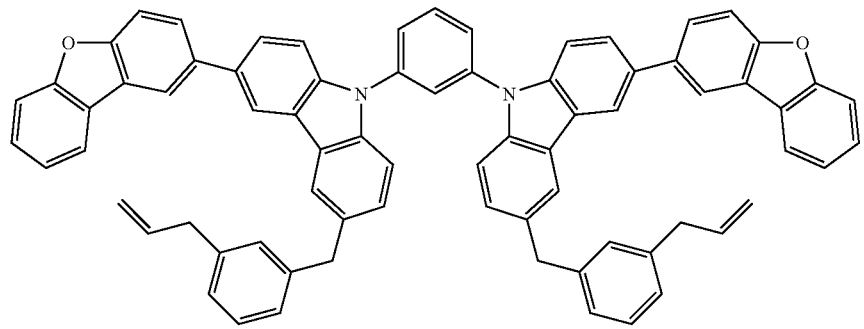
1-20
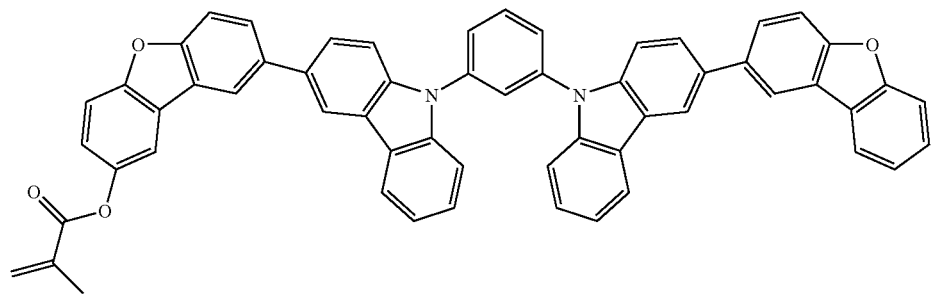
1-21 1-22
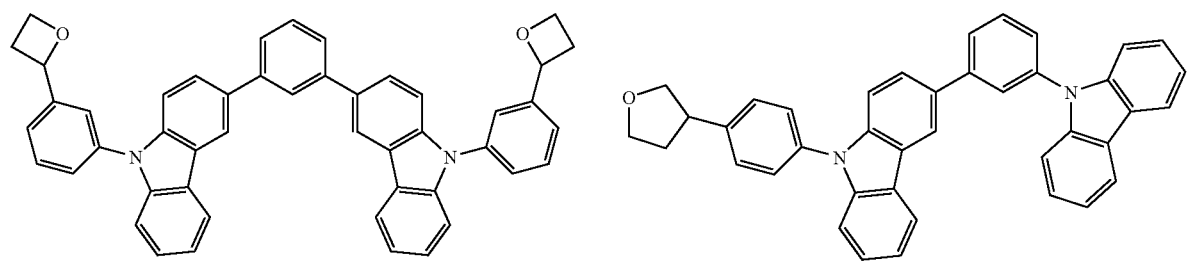
1-23 1-24
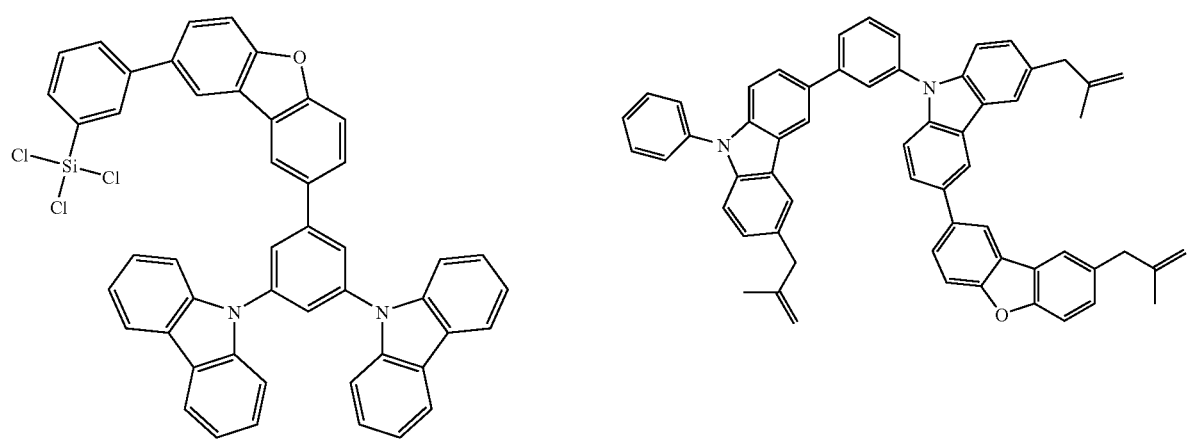

-continued
1-25
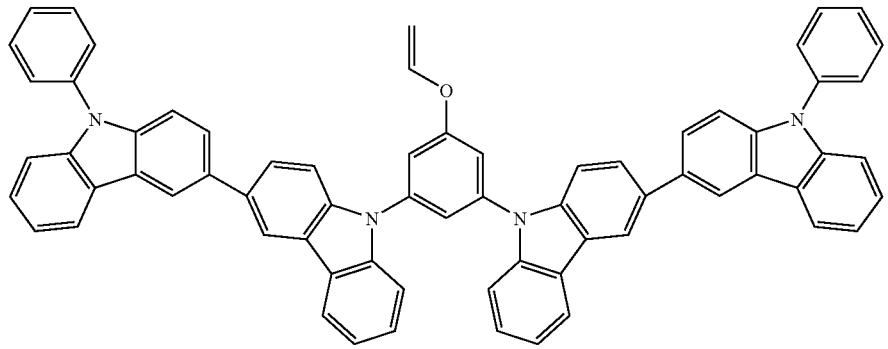
1-26
1-27
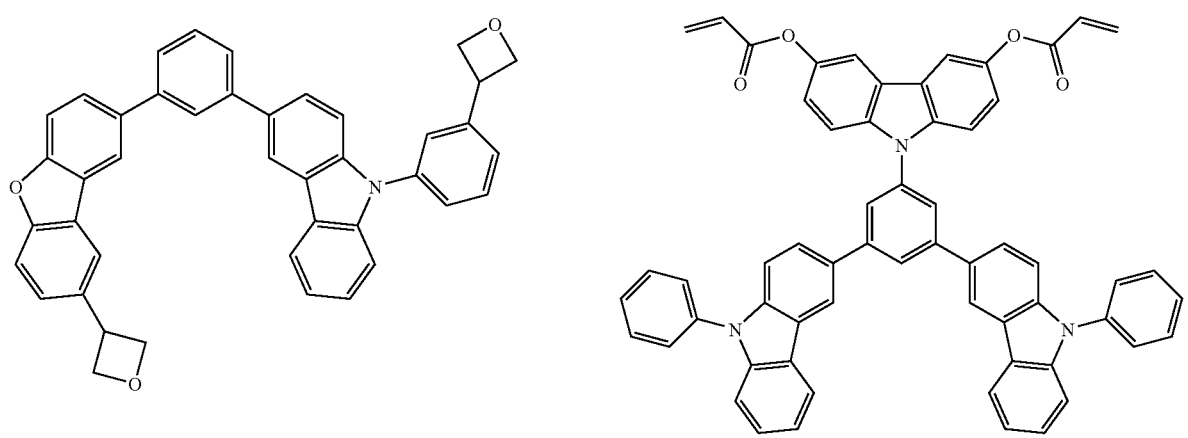
1-28
1-29
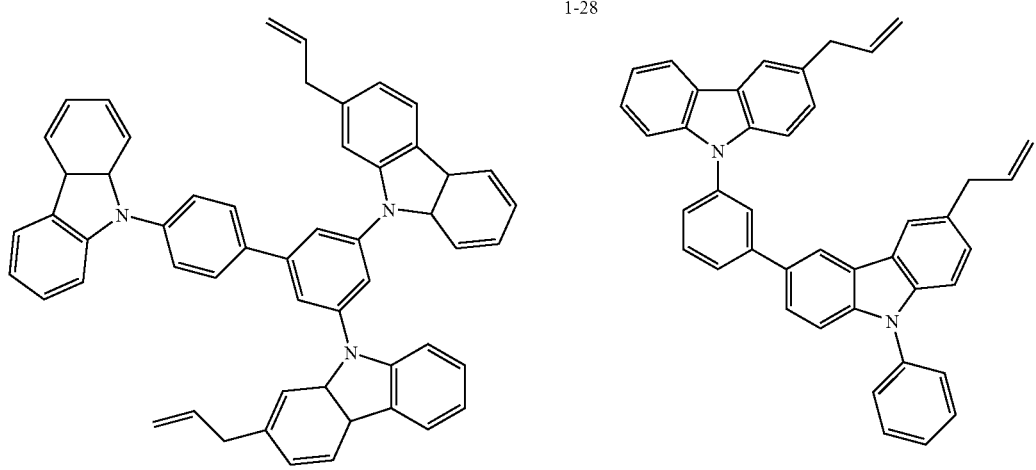

-continued
1-30
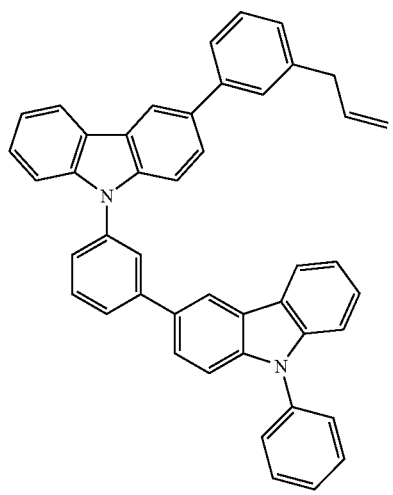
1-31
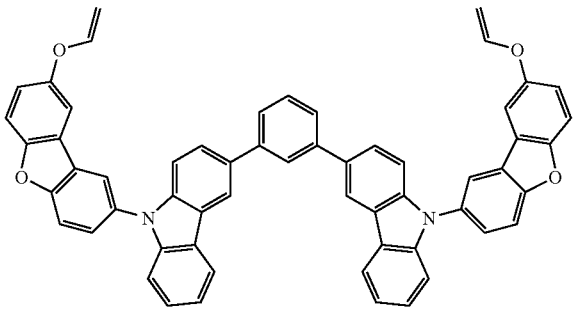
1-32
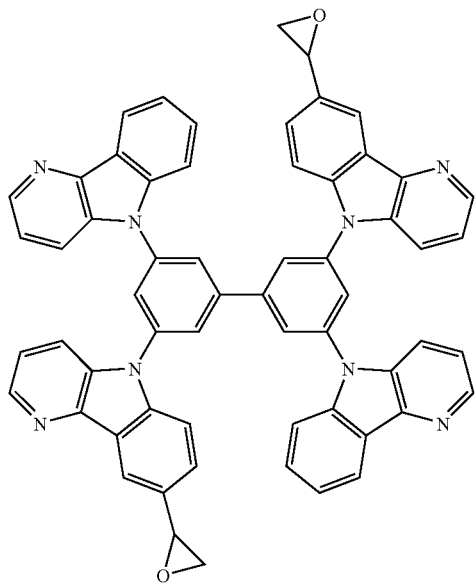
1-33
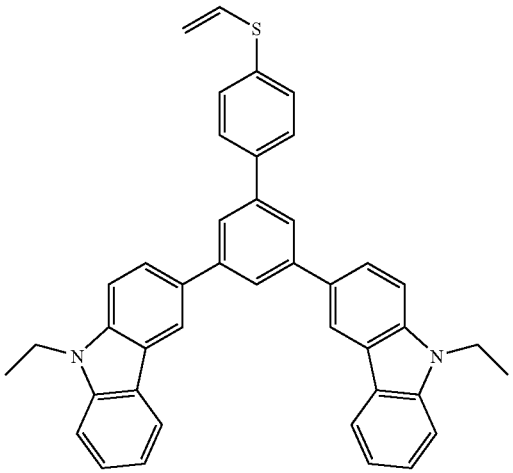
1-34
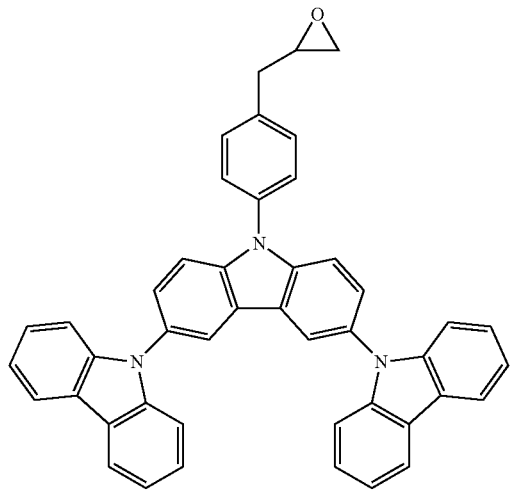
1-35

1-36
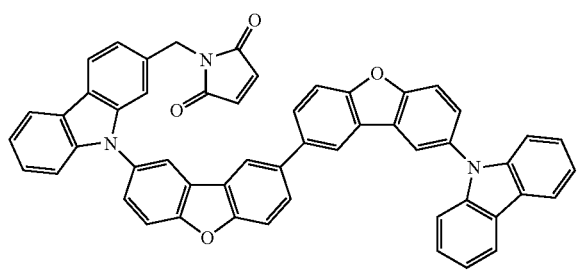
1-37
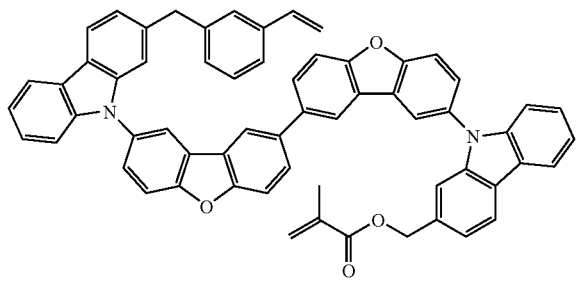
1-38
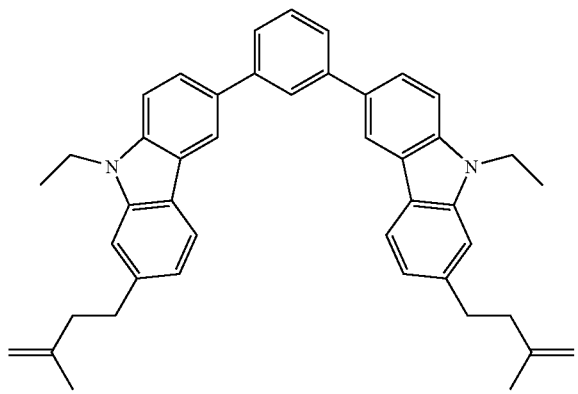
1-39
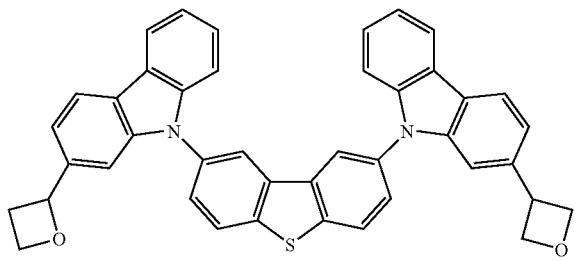
1-40
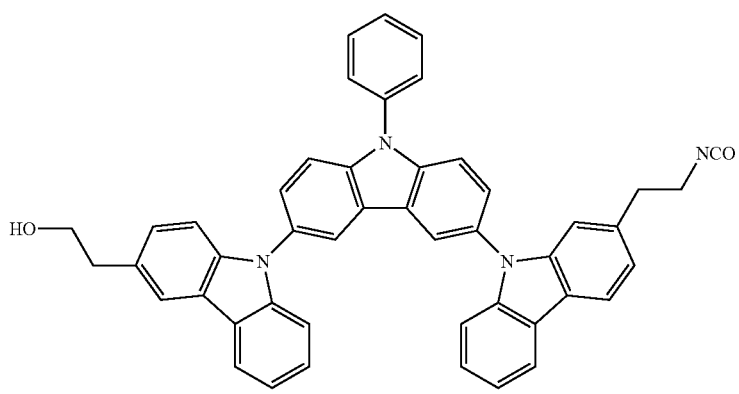

1-41
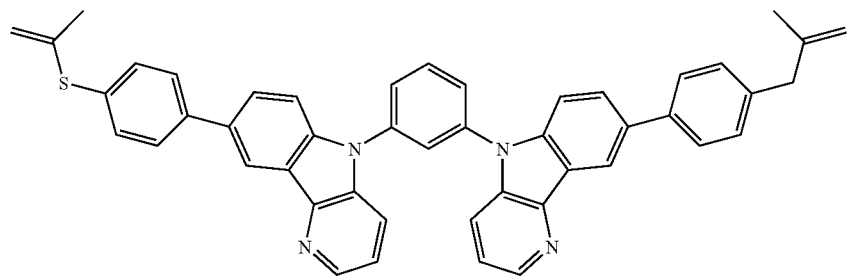
1-42 1-43
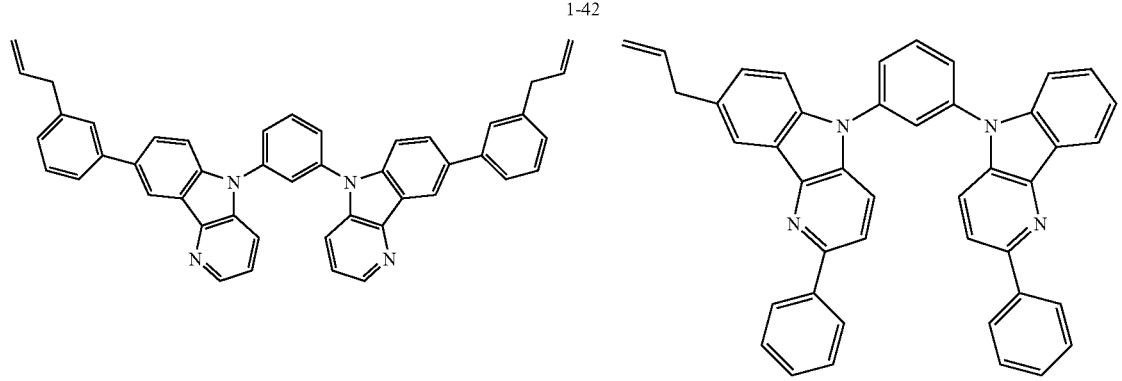
1-44 1-45
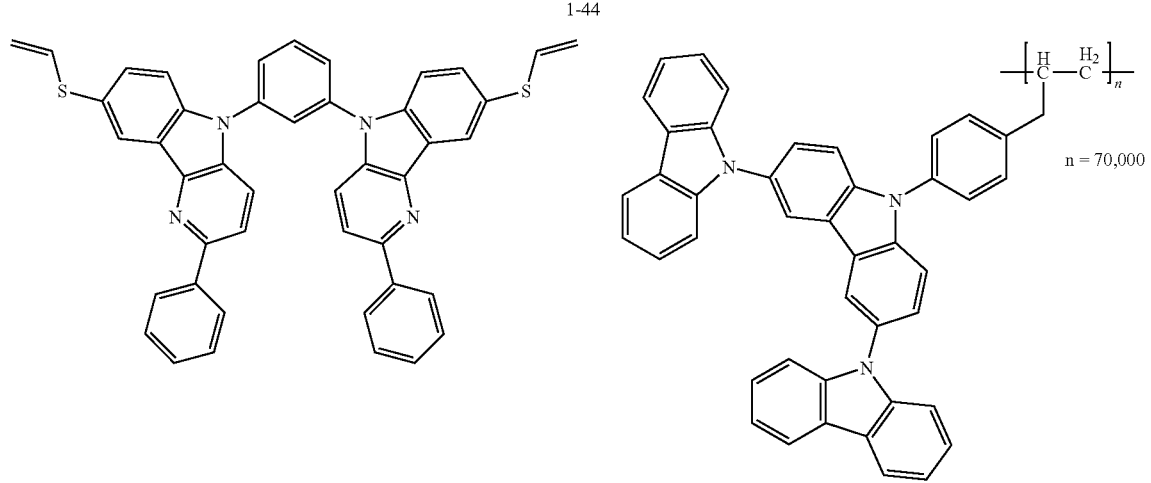

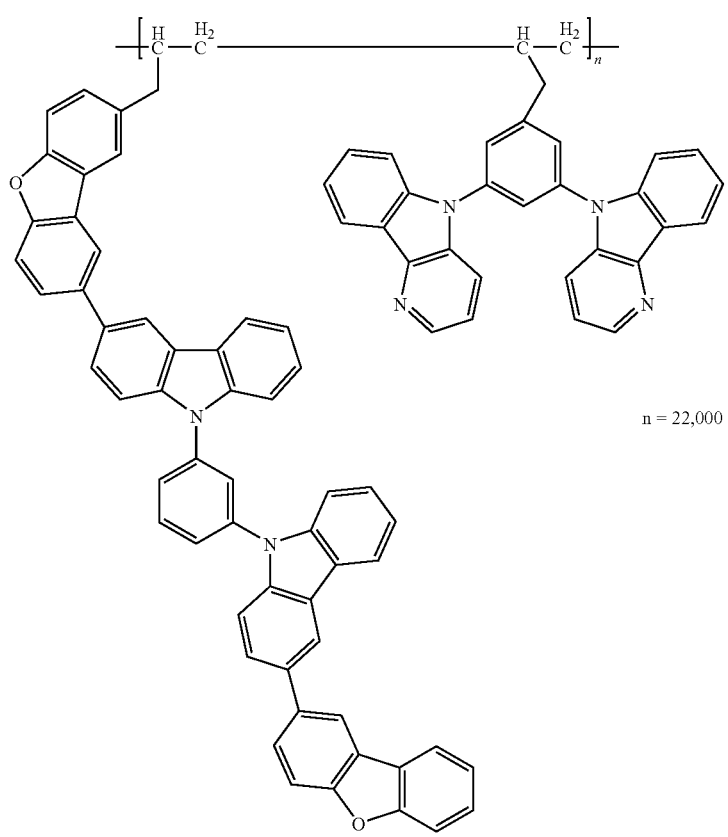

n = 22,000

1-46

The compound and its polymer described above can be synthesized by referring to published documents such as "Shin Kobunshi Jikkengaku 2, Kobunshi no Gousei Hanno" (New polymer experimental 2, Synthesize and reaction) by Kyoritsu Shuppan Kabusikikaisha.

Emitting Dopant

As an emitting dopant used in this invention, a fluorescent dopant or a phosphorescence dopant are employed. The emitting dopant employed in the emitting layer or emitting unit of the organic EL element according to this invention preferably contains a phosphorescence dopant as well as the host compound described above.

Phosphorescence Emitting Dopant

The phosphorescence emitting material is a compound which emits light from the excited triplet, which is specifically a compound which emits phosphorescence at room temperature (25° C.), and is defined to exhibit a phosphorescent quantum yield at 25° C. of not less than 0.01, and the phosphorescent quantum yield at 25° C. is preferably not less than 0.1.

The phosphorescent quantum yield can be measured according to a method described in the fourth edition "Jikken Kagaku Koza 7", Bunko II, page 398 (1992) published by Maruzen. The phosphorescent quantum yield in a solution can be measured employing various kinds of solvents. The phosphorescence emitting material of the present invention is a compound, in which the phosphorescent quantum yield measured employing any one of the solvents falls within the above-described range (0.01 or more).

The light emission of the phosphorescence emitting material is divided in two types in principle, one is an energy transport type in which recombination of a carrier occurs on the host to which the carrier is transported to excite the host, the resulting energy is transported to the phosphorescent compound, and light is emitted from the phosphorescent compound, and the other is a carrier trap type in which recombination of a carrier occurs on the phosphorescent compound which is a carrier trap material, and light is emitted from the phosphorescent compound.

However, in each type, energy level of the phosphorescent compound in excited state is lower than that of the host in excited state.

The phosphorescence emitting material can be optionally selected from the known phosphorescence emitting materials used in the light emitting layer of an organic EL element.

The phosphorescence emitting material is preferably a complex containing a metal of Group 8-10 of the periodic table, and more preferably an iridium compound, an osmium compound, a platinum compound (a platinum complex compound) or a rare-earth metal complex. Of these, most preferable is an iridium compound.

The compounds having a reactive substituent described below are preferably employed as the phosphorescent emitting dopants according to this invention.

Specific examples of a compound used as a phosphorescence emitting material are shown below, however, the present invention is not limited thereto. These compounds can be synthesized, for example, according to a method described in Inorg. Chem., 40, 1704-1711.

Practical examples of the phosphorescent emitting dopants according to this invention are listed, but this invention is not limited thereto.

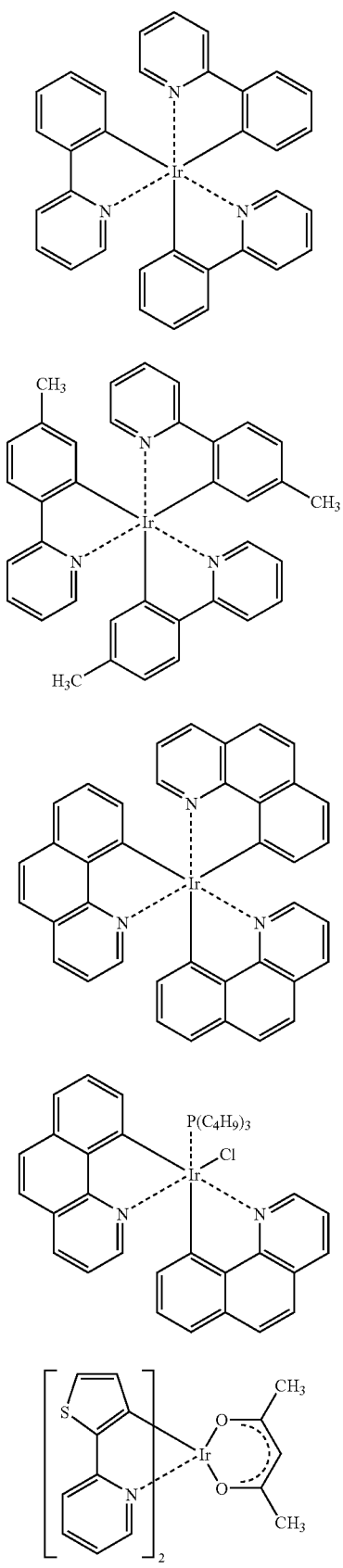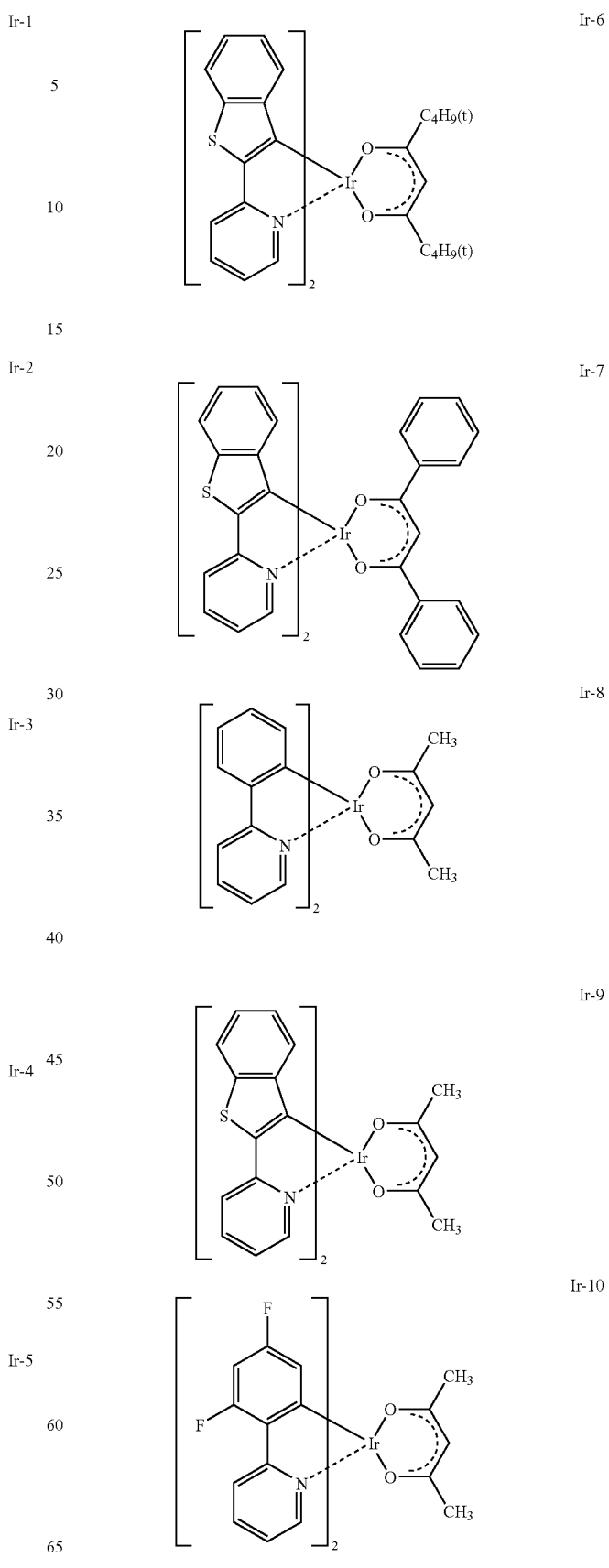

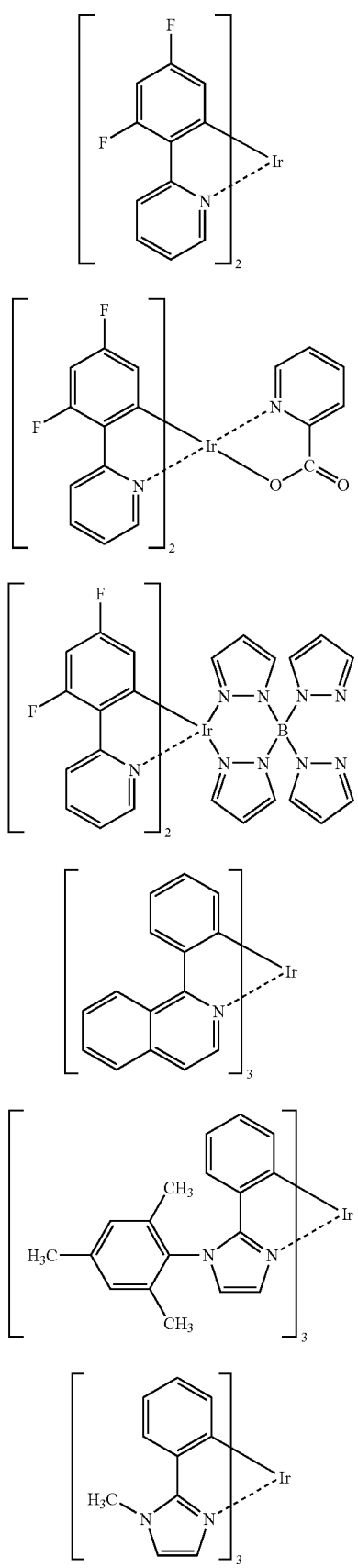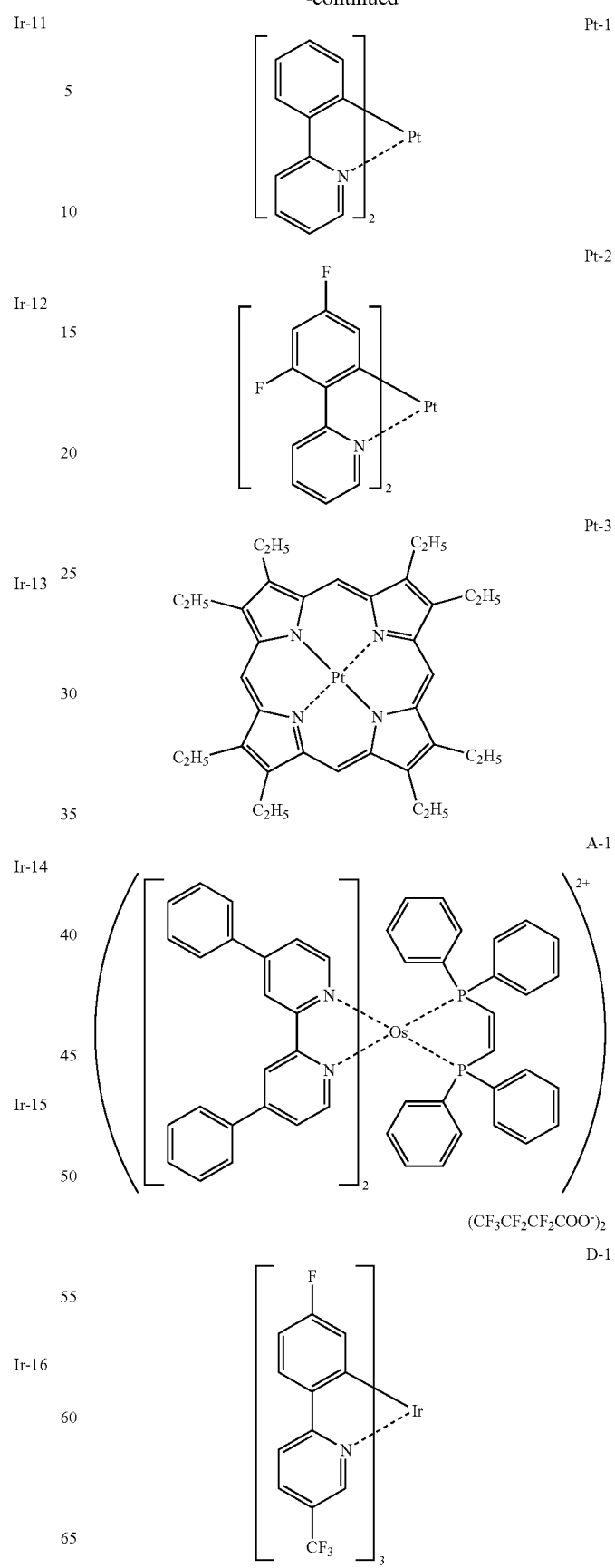

-continued
D-2
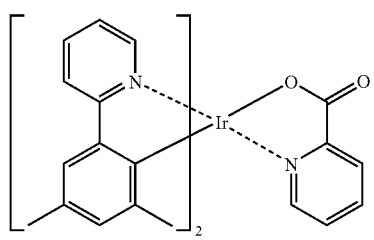
D-3
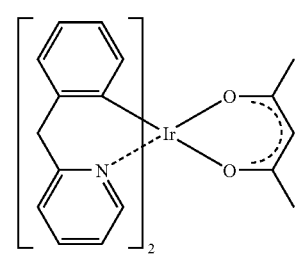
D-4
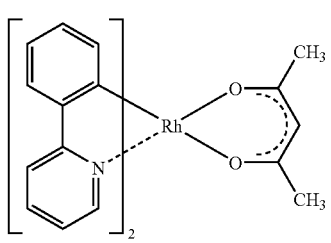
D-5
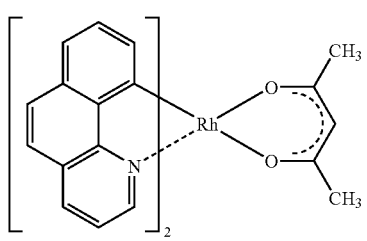
D-6
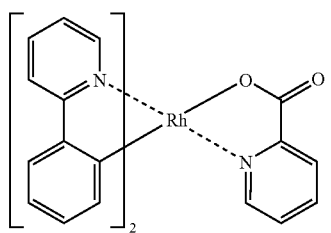
Pd-1
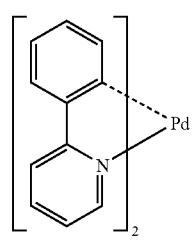
-continued
Pd-2
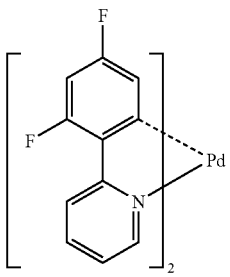
Pd-3
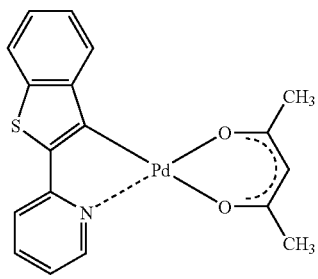
Rh-1
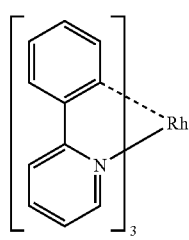
Rh-2
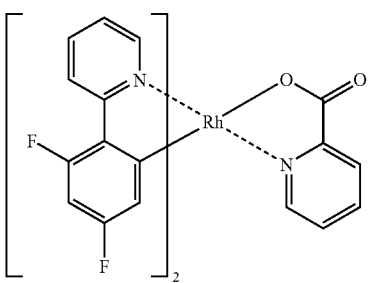
Rh-3
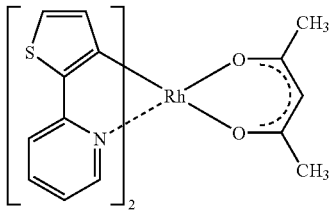
2-1
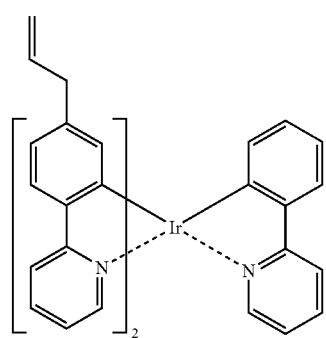

2-2
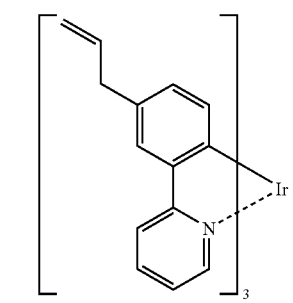
2-3
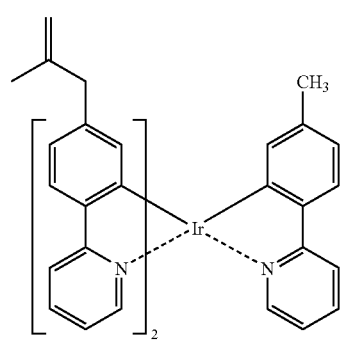
2-4
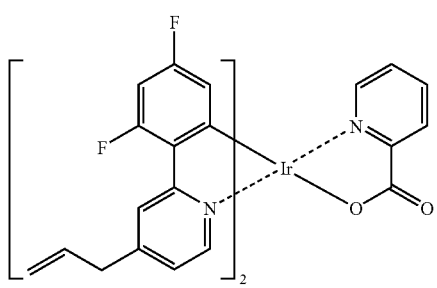
2-5
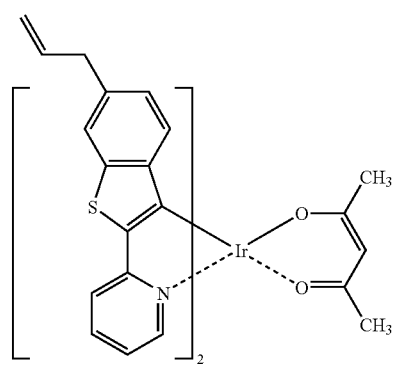
2-6
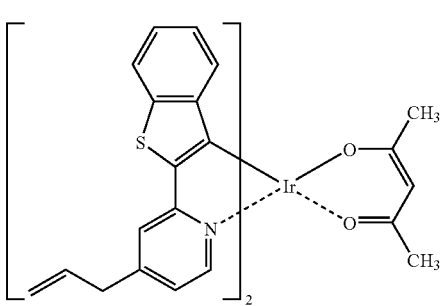
2-7
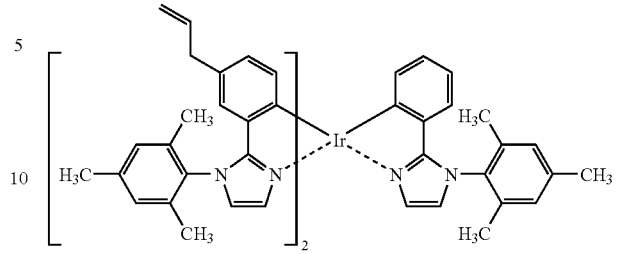
2-8
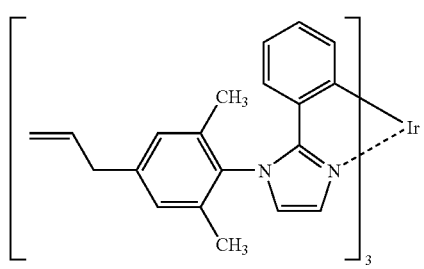
2-9
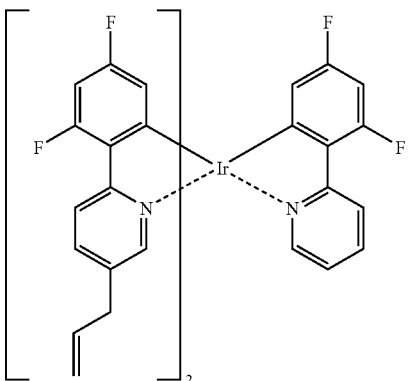
2-10
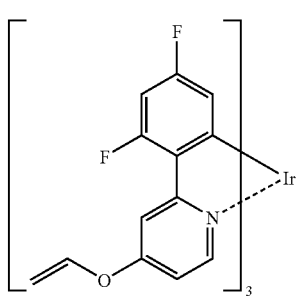

-continued 2-11
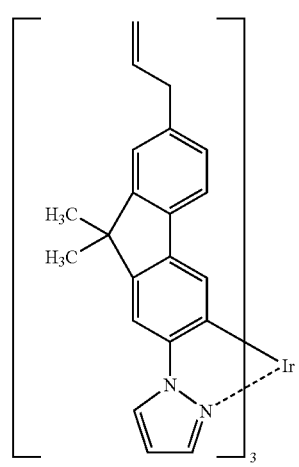

2-15
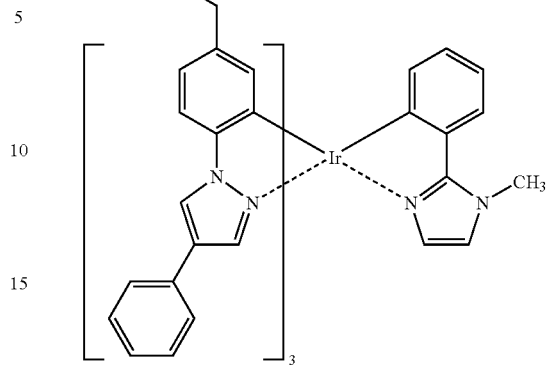

2-12
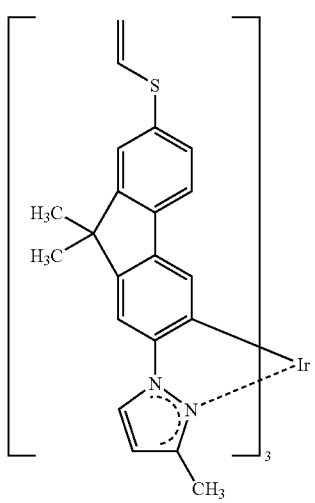

2-16
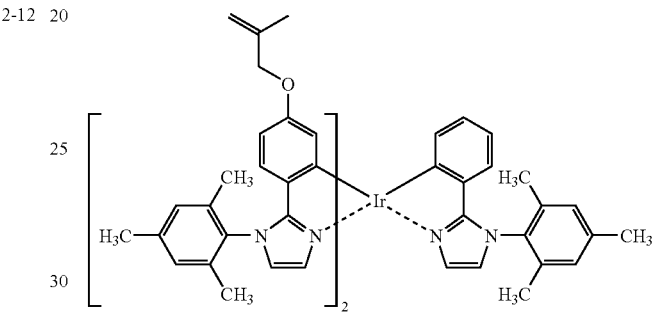

2-13

<Fluorescent Emitting Dopant>

A typical example of the fluorescent emitting dopant (a fluorescent dopant) includes coumarin type dye, pyran type dye, cyanine type dye, croconium type dye, squalium type dye, oxobenzanthracene type dye, fluorescein type dye, rhodamine type dye, pyrilium type dye, perylene type dye, stilbene type dye, polythiophene type dye or rare earth complex type fluorescent substances.

Next, an injection layer, an inhibition layer, an electron transport layer etc., employed as composition layers of the EL element of the present invention are described.

<<Injection Layer: Electron Injection Layer, Positive Hole Injection Layer>>

An injection layer is provided when it is necessary and includes an electron injection layer and a positive hole injection layer, which may be arranged between an anode and an emitting layer or a positive transport layer, and between a cathode and an emitting layer or an electron transport layer, as described above.

An injection layer is a layer which is arranged between an electrode and an organic layer to decrease an driving voltage and to improve an emission luminance, which is detailed in volume 2, chapter 2 (pp. 123-166) of "Organic EL Elements and Industrialization Front thereof (Nov. 30, 1998, published by N. T. S. Inc.)", and includes a positive hole injection layer (an anode buffer layer) and an electron injection layer (a cathode buffer layer).

An anode buffer layer (a positive hole injection layer) is also detailed in such as JP-A H09-45479, JP-A H09-260062 and JP-A H08-288069, and specific examples include such as a phthalocyanine buffer layer represented by such as copper phthalocyanine, an oxide buffer layer represented by such as vanadium oxide, an amorphous carbon buffer layer, and a polymer buffer layer employing conductive polymer such as polyaniline (emeraldine) and polythiophene.

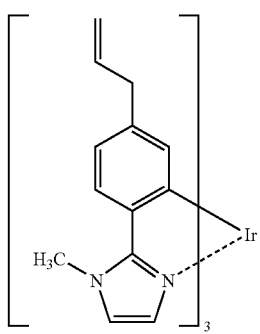

2-14
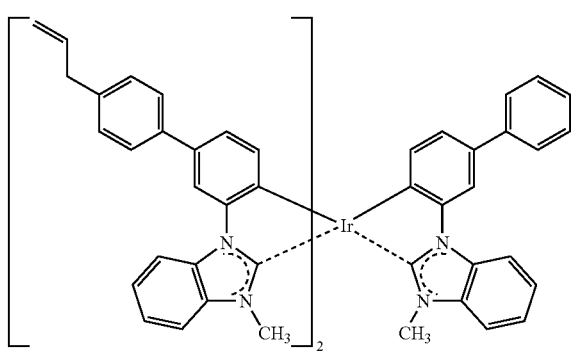

A cathode buffer layer (an electron injection layer) is also detailed in such as JP-A H06-325871, JP-A H09-17574 and JP-A H10-74586, and specific examples include a metal buffer layer represented by strontium, aluminum and so on, an alkali metal compound buffer layer represented by lithium fluoride, an alkali metal earth compound buffer layer represented by magnesium fluoride and an oxide buffer layer represented by aluminum oxide. The above-described buffer layer (injection layer) is preferably a very thin layer, and the layer thickness is preferably in a range of 0.1 nm-5 μm although it depends on a raw material.

<Inhibition Layer: Positive Hole Inhibition Layer, Electron Inhibition Layer>

An inhibition layer is provided in addition to an elemental layer arrangement of the organic compound layer as described above. There is, for example, a positive inhibition (hole block) layer described in such as JP-A H11-204258 and JP-A H11-204359 and p. 237 of "Organic EL Elements and Industrialization Front Thereof (Nov. 30, 1998), published by NTS. Inc.)".

A positive hole inhibition layer, in a broad meaning, is provided with a function of electron transport layer, being comprised of a material having a function of transporting an electron but a very small ability of transporting a positive hole, and can improve the recombination probability of an electron and a positive hole by inhibiting a positive hole while transporting an electron. Further, an arrangement of an electron transport layer described later can be appropriately utilized as a positive hole inhibition layer according to this invention.

The positive hole inhibition layer of the organic EL element of this invention is preferably provided adjacent to an emitting layer.

It is preferred that a positive hole inhibition layer contains an azacarbazole derivative recited as an example of a host compound.

When the element comprises a plural number of emitting layers of different emission colors, an emitting layer, an emission maximum wavelength of which is shortest, is preferably arranged nearest to an anode among the all emitting layers, however, in such a case, a hole block layer is preferably additionally arranged between said shortest wavelength layer and an emitting layer second nearest to an anode. Further, not less than 50 weight % of a compound contained in a hole block layer arranged at said position has a larger ionization potential by not less than 0.3 eV against a host compound of the aforesaid shortest wavelength layer.

An ionization potential is defined by an energy required to release an electron existing on the HOMO (highest occupied molecular orbit) level to a vacuum level, and for example, can be determined according to the following method.

(1) By use of Gaussian 98 (Gaussian 98, Revision A. 11. 4, M. J. Frisch, et al, Gaussian, Inc., Pittsburgh Pa., 2002), which is a molecular orbit calculation software manufactured by Gaussian, Inc., USA; a value calculated by performing structural optimization (converted value of eV unit), the second place of decimals of which is rounded off, is defined as an ionization potential.

(2) An ionization potential can be also determined by being directly measured by means of photoelectron spectroscopy. For example, a low energy electron spectrometer "Model AC-1" manufactured by Riken Keiki Co., Ltd., or a method known as ultraviolet photoelectron spectroscopy can be preferably utilized.

On the other hand, an electron inhibition layer is, in a broad meaning, provided with a function of a positive hole transport layer, being comprised of a material having a function of transporting a positive hole but a very small ability of transporting an electron, and can improve the recombination probability of an electron and a positive hole by inhibiting an electron while transporting a positive hole. Further, an arrangement of a positive hole transport layer described later can be appropriately utilized as an electron inhibition layer. Thickness of the positive hole inhibition layer and electron transport layer is preferably 3 to 100 nm, and more preferably 5 to 30 nm.

<Positive Hole Transport Layer>

A positive hole transport layer contains a material having a function of transporting a positive hole, and in a broad meaning, a positive hole injection layer and an electron inhibition layer are also included in a positive hole transport layer. A single layer of or plural layers of a positive hole transport layer may be provided.

A positive hole transport material is those having any one of a property to inject or transport a positive hole or a barrier property to an electron, and may be either an organic material or an inorganic material. For example, listed are a triazole derivative, an oxadiazole derivative, an imidazole derivative, a polyarylalkane derivative, a pyrazoline derivative, a pyrazolone derivative, a phenylenediamine derivative, a arylamine derivative, an amino substituted chalcone derivative, an oxazole derivatives, a styrylanthracene derivative, a fluorenone derivative, a hydrazone derivative, a stilbene derivative, a silazane derivative, an aniline type copolymer, or conductive high molecular oligomer, specifically preferably such as thiophene oligomer.

As a positive hole transport material, those described above can be utilized, however, it is preferable to utilize a porphyrin compound, an aromatic tertiary amine compound and a styrylamine compound, and specifically preferably an aromatic tertiary amine compound.

Typical examples of an aromatic tertiary amine compound and a styrylamine compound include N,N,N',N'-tetraphenyl-4,4'-diaminophenyl; N,N'-diphenyl-N,N'-bis(3-methylphenyl)-(1,1'-biphenyl)-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-metylphenyl) phenylmethane; bis(4-di-p-tolylaminophenyl) phenylmethane; N,N'-diphenyl-N,N'-di(4-methoxyphenyl)-4,4'-diaminobiphenyl; N,N,N',N'-tetraphenyl-4,4'-diaminodiphenylether; 4,4'-bis(diphenylamino) quadriphenyl; N,N,N-trip-tolyl)amine; 4-(di-p-tolylamino)-4'-[4-(di-p-tolylamino)styryl]stilbene; 4-N,N-diphenylamino-(2-diphenylvinyl)benzene; 3-methoxy-4'-N,N-diphenylaminostilbenzen; and N-phenylcarbazole, in addition thereto, those having two condensed aromatic rings in a molecule described in U.S. Pat. No. 5,061,569, such as 4,4'-bis[N-(1-naphthyl)-N-phenylamino]biphenyl (NDP), and 4,4',4"-tris[N-(3-methylphenyl)-N-phenylamino]triphenylamine (MTDATA), in which three of triphenylamine units are bonded in a star burst form, described in JP-A H04-308688.

A polymer in which the material mentioned above is introduced in the polymer chain or a polymer having the material as the polymer main chain can be also used. As the hole injecting material or the hole transporting material, inorganic compounds such as p-type Si and p-type SiC are usable.

A so-called p-type hole blocking layer as disclosed in JP-A 11-251067 or described in the literature of J. Huang et al. (Applied Physics Letters 80(2002), p. 139) is also applicable.

In the present invention, these materials are preferably utilized since an emitting element exhibiting a higher efficiency is obtained.

This positive hole transport layer can be provided by forming a thin layer made of the above-described positive hole transport material according to a method known in the art such as a vacuum evaporation method, a spin coating method, a cast method, an inkjet method and a LB method. The layer thickness of a positive hole transport layer is not specifically limited, however, is generally 5 nm to 5 µm, and preferably 5 to 200 nm. This positive transport layer may have a single layer structure comprised of one or two or more types of the above described materials.

A positive hole transport layer having high p-type property doped with impurity can be utilized. Example thereof includes those described in JP-A H04-297076, JP-A 2000-196140, JP-A 2001-102175, and J. Appl. Phys., 95, 5773 (2004) and so on.

It is preferable to employ such a positive hole transport layer having high p-type property, since an element with lower power consumption can be prepared in this invention.

<Electron Transport Layer>

An electron transport layer is composed of a material having a function of transporting an electron, and in a broad meaning, an electron transport layer and a positive hole inhibition layer are also included in a positive hole transport layer. A single layer of or plural layers of an electron transport layer may be provided.

The electron transport material (it works as a positive hole inhibition layer, simultaneously), which is employed in a single electron transport layer and an electron transport layer provided adjacent to cathode side with respect to emitting layer when it is used as plural layers, is sufficient to have a function to transmit an electron injected from a cathode to an emitting layer, and compounds conventionally known in the art can be utilized by arbitrarily selection as a material thereof. Any one can be employed by selecting from conventionally known compounds as its material.

Examples of a material include such as a nitro-substituted fluorene derivative, a diphenylquinone derivative, a thiopyrandioxide derivative, carbodiimide, a fleorenylidenemethane derivative, anthraquinonedimethane and anthrone derivatives.

Further, a thiazole derivative in which an oxygen atom in the oxadiazole ring of the above-described oxadiazole derivative is substituted by a sulfur atom, and a quinoxaline derivative having a guinoxaline ring which is known as an electron attracting group can be utilized as an electron transport material. Polymer materials, in which these materials are introduced in a polymer chain or these materials form the main chain of polymer, can be also utilized.

Further, a metal complex of a 8-quinolinol derivative such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis(8-quinolinol)zinc (Znq); and metal complexes in which a central metal of the aforesaid metal complexes is substituted by In, Mg, Cu, Ca, Sn, Ga or Pb, can be also utilized as an electron transport material.

Further, metal-free or metal phthalocyanine, or those the terminal of which is substituted by an alkyl group and a sulfonic acid group, can be preferably utilized as an electron transport material. Further, distyrylpyrazine derivative, which has been exemplified as a material of an emitting layer, can be also utilized as an electron transport material, and, similarly to the case of a positive hole injection layer and a positive hole transport layer, an inorganic semiconductor such as an n-type-Si and an n-type-SiC can be also utilized as an electron transport material.

The electron transport layer can be provided by forming a thin layer made of the above-described electron transport material according to a method known in the art such as a vacuum evaporation method, a spin coating method, a cast method, an inkjet method and a LB method. The layer thickness of an electron transport layer is not specifically limited; however, is generally 5 nm-5 µm, preferably 5-200 nm. This electron transport layer may have a single layer structure comprised of one or not less than two types of the above described materials.

An electron transport layer having high n-type property doped with impurity can be utilized. Example thereof includes those described in JP-A H04-297076, JP-A H10-270172, JP-A 2000-196140, JP-A 2001-102175, and J. Appl. Phys., 95, 5773 (2004) and so on.

It is preferable to employ such an electron transport layer having high n-type property, since an element with lower power consumption can be prepared in this invention.

<Anode>

As an anode according to an organic EL element of this invention, those comprising metal, alloy, a conductive compound, which has a large work function (not less than 4 eV), and a mixture thereof as an electrode substance are preferably utilized.

Specific examples of such an electrode substance include a conductive transparent material such as metal like Au, CuI, indium tin oxide (ITO), $SnO_2$ and ZnO.

Further, a material such as IDIXO ($In_2O_3$—ZnO), which can prepare an amorphous and transparent electrode, may be also utilized. As for an anode, these electrode substances may be made into a thin layer by a method such as evaporation or spattering and a pattern of a desired form may be formed by means of photolithography, or in the case of requirement of pattern precision is not so severe (not less than 100 µm), a pattern may be formed through a mask of a desired form at the time of evaporation or spattering of the above-described substance.

When emission is taken out of this anode, the transmittance is preferably set to not less than 10% and the sheet resistance as an anode is preferably not more than a several hundreds $\Omega/\square$. Further, although the layer thickness depends on a material, it is generally selected in a range of 10-1,000 nm and preferably 10-200 nm.

<Cathode>

On the other hand, as a cathode according to this invention, metal, alloy, a conductive compound and a mixture thereof, which have a small work function (not more than 4 eV), are utilized as an electrode substance. Specific examples of such an electrode substance includes such as sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture and rare earth metal.

Among them, with respect to an electron injection property and durability against such as oxidation, preferable are a mixture of electron injecting metal with the second metal which is stable metal having a work function larger than electron injecting metal, such as a magnesium/silver mixture, a magnesium/aluminum mixture, a magnesium/indium mixture, an aluminum/aluminum oxide ($Al_2O_3$) mixture and a lithium/aluminum mixture, and aluminum.

A cathode can be provided by a method such as evaporation or spattering to form a thin layer. Further, the sheet resistance as a cathode is preferably not more than a several hundreds Ω/□ and the layer thickness is generally selected in a range of 10 nm-5 μm and preferably of 50-200 nm. Herein, to transmit emission, either one of an anode or a cathode of an organic EL element is preferably transparent or translucent to improve the emission luminance.

A transparent or translucent cathode may be prepared by a method in which the above mentioned metal is provided on the anode with a thickness of 1 to 20 nm and then electroconductive transparent material described as the anode. An element having both transparent anode and cathode may be prepared by applying this method.

<Substrate>

A substrate (also referred to as Base Body, Base Plate, Base Material or Support) according to an organic EL element of this invention is not specifically limited with respect to types of such as glass and plastics being transparent or opaque, however, a substrate preferably utilized includes such as glass, quartz and transparent resin film. A specifically preferable substrate is resin film capable of providing an organic EL element with a flexible property.

Resin film includes polyester such as polyethylene terephthalate (PET) and polyethylene naphthalate (PEN), polyethylene, polypropylene, cellophane, cellulose ester and its derivatives such as cellulose diacetate, cellulose triacetate, cellulose acetate butylate, cellulose acetate propionate (CAP), cellulose acetate phthalate (TAC), and cellulose nitrate, polyvinylidene chloride, polyvinylalcohol, polyethylenevinylalcohol, syndiotactic polystyrene, polycarbonate, norbornane resin, polymethylpentene, polyetherketone, polyimide, polyether sulfone (PES), polyphenylene sulfide, polysulfones, polyether imide, polyetherketone imide, polyimide, fluorine resin, nylon, polymethyl methacrylate, acryl or acrylates, cyclo-olefin resin such as ARTON (commercial name, manufactured by JSR Corp.) or APEL (commercial name, manufactured by Mitsui Chemicals Inc.).

On the surface of resin film, an inorganic or organic cover layer or a hybrid cover layer comprising the both may be formed, and the film is preferably provided with a high barrier ability having a vapor permeability of not more than 0.01 g/m$^2$·24 hr (at 25±0.5° C., 90±2% RH) measured by a method stipulated by JIS K 7129-1992, and more preferably a high barrier ability having an oxygen permeability of not more than 10$^{-3}$ ml/(m$^2$·24 hr·MPa) as well as a vapor permeability of not more than 10$^{-5}$ g/m$^2$·24 hr, measured by a method stipulated by JIS K 7126-1987.

Any materials capable of preventing penetration of substance causing degradation of the element such as moisture and oxygen are usable for forming the barrier layer. For example, silicon oxide, silicon dioxide and silicon nitride are usable. It is more preferable to give a laminated layer structure composed of such the inorganic layer and a layer of an organic material to the barrier layer for improving the fragility of the layer. It is preferable that the both kinds of layers are alternatively piled for several times though there is no limitation as to the laminating order of the inorganic layer and the organic layer.

The method for forming the barrier layer is not specifically limited and, for example, a vacuum deposition method, spattering method, reaction spattering method, molecule beam epitaxy method, cluster-ion beam method, ion plating method, plasma polymerization method, atmosphere pressure plasma polymerization method, plasma CVD method, laser CVD method, heat CVD method and coating method are applicable, and the atmosphere pressure plasma polymerization method such as that described in JP A 2004-68143 is particularly preferable.

As the opaque substrate, for example, a plate of metal such as aluminum and stainless steel, a film or plate of opaque resin and a ceramic substrate are cited.

External quantum efficiency of an organic EL element of the present invention at room temperature is preferably not less than 1%, and more preferably not less than 5%. Herein, external quantum efficiency (%)=a number of photons emitted outside of an organic EL element/a number of electrons flown in an organic EL element×100.

Further, a hue improving filter such as a color filter may be utilized together, and a color conversion filter, which converts emission color from an organic EL element into multicolor by use of a fluorescent substance, may be also utilized together. In the case of utilizing a color conversion filter, λmax of emission of an organic EL element is preferably not more than 480 nm.

<<Sealing>>

As the sealing means, a method for pasting together with a sealing material, the electrodes and the substrate by an adhesive agent is applicable.

The sealing material is placed so as to cover the displaying area of the organic EL element and may have a flat plate shape or a concave plate shape, and the transparence and the electric insulation property of it are not specifically limited.

A glass plate, polymer plate, polymer film, metal plate and metal film can be cited. As the glass plate, a plate of soda-lime glass, barium strontium-containing glass, lead glass, alumina silicate glass, boron silicate glass and quartz are usable practically.

As the polymer plate, a plate of polycarbonate, acryl resin, poly(ethylene terephthalate), polyether sulfide and polysulfone are usable. As the metal plate, a plate composed of one or more kinds of metal selected from stainless steel, iron, copper, aluminum, magnesium, nickel, zinc, chromium, titanium, molybdenum, silicon, germanium and tantalum and an alloy of them are cited.

The polymer film and the metal film are preferably used by which the element can be made thinner in this invention. The polymer film having an oxygen permeability of not more than 1×10$^{-3}$ ml/(m$^2$·24 hr·MPa), measured by a method stipulated by JIS K 7126-1987, and a vapor permeability of not more than 1×10$^{-5}$ g/m$^2$·24 hr (at 25±0.5° C., 90±2% RH) measured by a method stipulated by JIS K 7129-1992.

A sandblast treatment and a chemical etching treatment are applicable for making the sealing material into the concave shape.

A photo-curable and thermo-curable adhesive agents containing a reactive vinyl group of acryl type oligomer and a methacryl type oligomer, and a moisture curable adhesive agent such as 2-cyanoacrylate can be cited as the adhesive agent. Epoxy type thermally and chemically (two liquid type) curable adhesive agents are applicable. Hot-melt type polyamide, polyester and polyolefin adhesive agents are applicable. Cationic curable type UV curable epoxy adhesive agent is also usable.

The organic EL element is degraded by heat in some cases, therefore, the adhesive agent capable of being cured to adhere within the temperature range of from room temperature to 80° is preferred. A moisture absorbing agent may be dispersed in the adhesive agent. Coating of the adhesive agent onto the adhering portion may be performed by a dispenser available on the market or printing by a screen printing.

It is preferable that an inorganic or organic layer is provided on outside of the electrode placed on the side of facing to the substrate through an organic layer so as to cover the electrode and the organic layer and contact with the substrate to form a sealing layer. In such the case, the material for forming the sealing layer may be a material having a function to inhibit permeation of a substance causing degradation such as water and oxygen, and silicon oxide, silicon dioxide and silicon nitride are usable for example. The layer preferably has a laminated structure composed of an inorganic material and an organic material.

In the space between the sealing material and the displaying portion of the organic EL element, an inactive gas such as nitrogen and argon or an inactive liquid such as silicone oil is preferably injected. The space may be made vacuum. A moisture absorbing compound may be enclosed in the element.

Examples of the moisture absorbing compound include a metal oxide such as sodium oxide, potassium oxide, calcium oxide, barium oxide, magnesium oxide and aluminum oxide, a sulfate such as sodium sulfate, calcium sulfate, magnesium sulfate and cobalt sulfate, a metal halide such as calcium chloride, magnesium chloride, cesium fluoride, tantalum fluoride, cerium bromide, magnesium bromide, barium iodide and magnesium iodide, and a perchlorate such as barium perchlorate and magnesium perchlorate. Anhydrate is preferable as to the sulfate, halide and perchlorate.

<<Protection Layer and Protection Plate>>

For raising the mechanical strength of the element, a protection layer or a protection plate may be provided on outside of the sealing layer of the side facing to the substrate through the organic layer or the outside of the sealing film. Such the protection layer or plate is preferably provided since the strength of the element is not always so high when the sealing is carried out by the foregoing sealing layer. The glass plate, polymer plate, polymer film and plate, and metal film and plate the same as those to be used for sealing are usable for such the protection material. Polymer film is preferably used from the viewpoint of light weight and less thickness.

<Preparation Method of Organic EL Element>

As an example of a preparation method of an organic EL element of this invention, a preparation method of an organic EL element, comprising anode/positive hole injection layer/positive hole transport layer/emitting layer/positive hole inhibition layer/electron transport layer/cathode, will be described.

First, on an appropriate substrate, a thin layer comprising a desired electrode substance such as an anode electrode substance is formed by means of coating according to this invention including uniform coating or coating using dispersion, evaporation or spattering so as to make a layer thickness of not more than 1 μm and preferably of 10-200 nm, whereby an anode is prepared. Next, thin layers containing organic substances of such as a positive hole injection layer, a positive hole transport layer, an emitting layer, a positive hole inhibition layer and an electron transport layer are formed on this layer. Coating, vapor deposition, sputtering and so on can be employed to form a cathode similarly to that of an anode as described above.

After formation of these layers, a thin layer comprising a cathode electrode substance is formed thereon by means of such as evaporation or spattering so as to make a layer thickness of 1 mm or less, preferably 50-200 nm to provide a cathode, whereby a desired organic EL element can be prepared. The organic EL element is preferably manufactured by a process in which the hole injection layer through the cathode are prepared during one evacuation process. However, it may be taken out during procedure and different layer forming method can be applied. The process is necessary to conduct in a circumstance of dry inert gas.

A shadow mask is provided in a process of forming emitting layer in the multicolor display device employing the organic EL element of this invention, and patterning such as the shadow mask is not necessary because the other layers are common. These layers are formed by a method such as cast method, spin coating, ink jet method, spray method, printing method and so on.

Further, reversing the preparation order, it is also possible to prepare layers in the order of a cathode, an electron transport layer, a positive hole inhibition layer, an emitting layer, a positive hole transport layer and an anode. When a direct current voltage is applied on the multicolor display device thus prepared, emission can be observed by application of a voltage of approximately 2 to 40 V setting an anode to + (plus) polarity and a cathode to − (minus) polarity. Further, no current flows and no emission generate at all even when a voltage is applied with a reversed polarity. Further, in the case of alternate current voltage being applied, emission generates only in a state of an anode being + and a cathode being −. Herein, the wave shape of alternate current may be arbitrary.

An evaporation method or coating method is employed to form an anode, cathode and organic or inorganic layer provided between the anode and the cathode. A coating method, including solution coating and dispersion coating, is preferably employed for forming the organic or inorganic layer provided between the anode and the cathode.

The coating method includes so called wet process such as a spin coat method, a cast method, an inkjet method and a the printing method, and spin coat method, the inkjet method the printing method and so on are preferably employed to form a uniform layer without occurring pinhole. Different layer forming method can be applied for each layer.

Thickness of each of the organic or inorganic layer is 0.1 nm to 5 μm, and preferably is optionally selected within 5 to 200 nm.

Vapor deposition method may be applied in combination to form a composition layer of the organic EL element such as an anode, a cathode, an organic layer or inorganic layer. The vapor condition, which varies depending on the species of compounds, is preferably adjusted so that the temperature for boat heating is 50 to 450° C., degree of vacuum of $10^{-6}$ to $10^{-2}$ Pa, rate of vapor deposition is 0.01 to 50 nm/sec, and temperature of the substrate of −50 to 300° C.

In a coating method for producing the organic EL element according to this invention, it is allowed that coating composition of the organic EL element as used may be solution in which the composition materials are uniformly dissolved or dispersion in which the composition materials of the organic layer are dispersed as a solid component. At least two layers of the organic layers of the organic EL element are formed by a coating method, and at least one layer other than a layer contacting to the anode is formed by employing dispersion coating composition.

The coating composition according to this invention includes solution in which optionally selected materials for forming a cathode, an anode and an organic layer are dissolved in a solvent and dispersion in which particles (primary particles or secondary particles) of optionally selected materials for forming a cathode, an anode and an organic layer are dispersed in a solvent.

Taking Out Light

Generally it is said that, in the organic EL element of this invention, light is emitted in a layer of which refractive index is higher (the refractive index is about 1.7 to 2.1) than that of air, and only 15 to 20% of the light emitted in the light emitting layer can be taken out. This is because the light which enters into the interface (interface of a transparent substrate and air) with the angle θ larger than a critical angle cannot be taken out of the element due to the total internal reflection, or because the light is totally reflected between the transparent substrate and the transparent electrode or between the transparent substrate and the light emitting layer, resulting in being wave-guided in the transparent electrode or in the light emitting layer to get away to the side of the element.

Examples of a method to improve the efficiency of taking out of the light include: a method to form concavity and convexity on the surface of the transparent substrate to prevent total internal reflection at the interface between the transparent substrate and air (for example, refer to U.S. Pat. No. 4,774,435); a method to provide a light converging function to the substrate (for example, refer to JP-A S63-314795); a method to provide a reflecting surface on the side of the element (for example, refer to JP-A No. 01-220394); a method to provide a flat layer between the substrate and the light emitting layer, the flat layer having an intermediate refractive index to form an anti-reflection layer (for example, refer to JP-A S62-172691); a method to provide a flat layer having a low refractive index between the substrate and the light emitting layer (for example, JP-A 2001-202827); and a method to provide a diffraction grating between any of the substrate, transparent electrode and light emitting layer (including the interlayer between the substrate and out side air) (for example refer to JP-A H11-283751).

These methods can be used in combination with the organic electroluminescence element of the present invention. Also, a method of forming a flat layer having a lower refractive index than that of the substrate between the substrate and the light emitting layer, or a method of forming a diffraction grating between any of the substrate, transparent electrode and light emitting layer (including the interlayer between the substrate and out side air) can be preferably used.

As a low refractive index layer, earogel, porous silica, magnesium fluoride and fluorine-containing polymer, are cited, for example. Since the refractive index of the transparent substrate is generally 1.5 to 1.7, the refractive index of the low refractive index layer is preferably 1.5 or less and more preferably 1.35 or less.

The thickness of a low refractive index medium is preferably more than twice of the wavelength of the light in the medium, because when the thickness of the low refractive index medium, where the electromagnetic wave exuded as an evanescent wave enters into the transparent substrate, and the effect of the low refractive index layer is reduced.

The method to provide a diffraction grating at the interface where the total internal reflection occurs or in some of the medium has a feature that the effect of enhancing the light-extracting efficiency is high. The intention of this method is to take out the light which cannot come out due to such as total internal reflection between the layers among the light emitted in the light emitting layer, by providing a diffraction grating between any of the layers or in any of the mediums (in the transparent substrate or in the transparent electrode), using the property of the diffraction grating that it can change the direction of light to a specified direction different from the direction of reflection due to so-called Bragg diffraction such as primary diffraction or secondary diffraction.

The diffraction grating to be provided preferably has a two-dimensional periodic refractive index. This is because, since the light is emitted randomly to any direction, only the light proceeds to a specific direction can be diffracted when a generally used one-dimensional diffraction grating having a periodic refractive index only in a specific direction is used, whereby the light-extracting efficiency is not largely increases. However, by using diffraction grating having a two-dimensionally periodic refractive index, the light proceeds any direction can be diffracted, whereby the light-extracting efficiency is increased.

The diffraction grating may be provided between any of the layers on in any of the mediums (in the transparent substrate or in the transparent electrode), however, it is preferably provided in the vicinity of the organic light emitting layer where the light is emitted. The period of the diffraction grating is preferably ½ to 3 times of the wavelength of the light in the medium. The array of the diffraction grating is preferably two-dimensionally repeated, for example, as in the shape of a square lattice, a triangular lattice, or a honeycomb lattice.

<<Light-Condensing Sheet>>

In the organic electroluminescence element of the present invention, the luminance in the specified direction, for example, the front direction against the emitting plane of the element can be increased, for example, by processing to form a structure of a micro-lens array or in combination with a so-called light-condensing sheet on the light-extracting side surface of the substrate.

As an example of a micro-lens array, quadrangular pyramids 30 μm on a side and having a vertex angle of 90° are two-dimensionally arranged on the light extracting side surface of the substrate. The side of the quadrangular pyramids is preferably 10 to 100 μm. When the length of the side is shorter than the above range, the light is colored due to the effect of diffraction, and when it is longer than the above range, it becomes unfavorably thick.

As a light-condensing sheet, the one practically applied for an LED backlight of a liquid crystal display is applicable. Examples of such a sheet include a brightness enhancing film (BEF) produced by SUMITOMO 3M Inc. As the shape of the prism, triangle-shaped strip having a vertex angle of 90° and a pitch of 50 μm, the one having round apexes, or the one having a randomly changed pitch may be included.

In order to control the luminous radiation angle of the light emitting element, a light diffusion plate and a film may be used in combination with the light-condensing sheet. For example, a diffusion film (light-up) produced by KIMOTO Co., Ltd. can be used.

The organic EL element of the invention can be used as a displaying device and various kinds of light source. As the light source, domestic illumination, car interior illumination, backlight of watches or liquid crystal displays, sign boards, signals, light source of photo memories, light source of electrophotographic copying machine, light source of light communication processor and light source of light sensors though the use is not limited to the above. Particularly, the device is suitably used in combination with a color filter as the backlight of the liquid crystal display or the light source of illumination.

<<Display Device>>

The display device of this invention is described. The display device of this invention is used for a multicolor or white display device. A shadow mask is provided only when an emitting layer is formed in case of a multicolor or white display device. When the emitting layer is subjected to patterning, the patterning method is not limited but is preferably a vapor deposition, inkjet and printing method. The patterning employing a shadow mask is preferable when the evaporation method id employed.

When a direct current voltage is applied on the multicolor display device thus prepared, emission can be observed by application of a voltage of approximately 2 to 40 V setting an anode to plus polarity and a cathode to minus polarity. No current flows and no emission generates at all even when a voltage is applied with a reversed polarity. In the case of alternate current voltage being applied, emission generates only in a state of an anode being plus and a cathode being minus. Herein, the wave shape of alternate current may be arbitrary.

<<Illumination Device>>

Further, an organic EL element of this invention may be utilized as one type of a lamp like an illumination and an exposure light, and may be also utilized as a display device of a projector of an image projecting type and a display device (a display) of a type to directly view still images and moving images. An operating mode in the case of being utilized as a display device for playback of moving images may be either a simple matrix (a passive matrix) mode or an active matrix mode.

An emitting material utilized in an emitting layer is not specifically limited, and in the case of a backlight of a liquid crystal display element, any combination by arbitrary selection among the emitting dopants or by combining the light takeout and/or condensing sheet so as to be fitted to the wavelength range corresponding to color filter characteristics, whereby white emission can be obtained.

The organic EL element is preferable since a color organic EL display with low voltage driving and long life characteristics can be obtained by combining a color filters or arranging the element and driving transistor circuit in accordance with color filter pattern so that blue light having maximum emission in a range of 430 to 480, green light having maximum emission in a range of 520 to 550, and red light having maximum emission in a range of 600 to 640 are obtained through a blue filter, a green filter and a red filter employing the white light taken out from the organic EL element as the backlight.

In this manner, a white emitting organic EL element of this invention is usefully utilized as one type of a lamp such as a home use illumination, a car room illumination or an exposure light source as various emission light sources or lighting devices, in addition to the above described display. Further it is applied to various uses such as a backlight of a watch etc., a signboard, a signal, a light source of a light memory medium, a light source of an electrophotographic printer, a light source of a light communication processor, a light source of a light sensor, and further general home use electric devices requiring a display device.

EXAMPLES

The present invention will now be described with reference to examples, however the present invention is not limited thereto.

Example 1

(Preparation of Comparative Sample 1-1)

A 100 mm×100 mm×1.1 mm quartz substrate was subjected to ultrasonic cleaning employing isopropyl alcohol, followed by drying via desiccated nitrogen gas and cleaning via UV ozone for 5 minutes, then was set on a spin coater obtained in the market. A solution, which was prepared by dissolving 30 mg of polyvinyl carbazole (PVCz) and 3 mg of Ir-1 dissolved in 10 ml of dichloroethane, was applied onto the substrate at 600 rpm for 30 seconds via a spin coating method, and a first organic layer was prepared.

A solution, which was prepared by dissolving 50 mg of (tBu)PBD and 3 mg of Ir-1 in 10 ml of solvent mixture of methanol and acetonitrile, ratio of methanol/acetonitrile being 85/15 was applied onto the substrate at 1,500 rpm for 30 seconds via a spin coating method to form a second organic layer on the first organic layer, and Comparative Sample 1-1 was prepared.

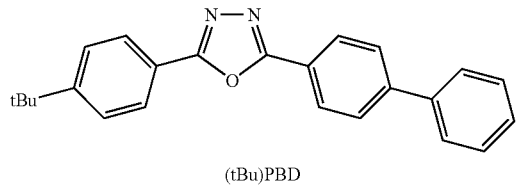

(tBu)PBD (Preparation of Inventive Sample 1-2)

The first organic layer was prepared in the same way as Comparative Sample 1-1.

Then a solution was prepared by dissolving 5 mg of Ir-1 in 1 L of solvent mixture of methanol and acetonitrile, ratio of methanol/acetonitrile being 85/15, and a coating solution of the second organic layer was prepared by dissolving 50 mg of (tBu)PBD in 10 ml of the obtained solution. This coating solution was applied onto the substrate at 1,500 rpm for 30 seconds via a spin coating method on the first organic layer, and Inventive Sample 1-2 was prepared.

Distribution of Ir element in a direction of applied layers was measured via TOF-SIMS for each of the Comparative Sample 1-1 and the Inventive Sample 1-2. While iridium was not detected from the second organic layer of the Comparative Sample 1-1, iridium was detected from the second organic layer of the Inventive Sample 2-1 to confirm that the second organic layer contains a material composing the first organic layer.

Example 2

(Preparation of Organic EL Element 2-1, 2-2 and 2-3)

A substrate (NA-45, produced by NH Techno Glass Corp.), which was prepared in such a manner that ITO (indium tin oxide) was applied onto a 100 mm×100 mm×1.1 mm glass substrate to form a 100 nm thick film as an anode, was subjected to patterning. Thereafter, a transparent supporting substrate provided with the above ITO transparent electrode was subjected to ultrasonic cleaning employing isopropyl alcohol, followed by drying via desiccated nitrogen gas and cleaning via UV ozone for 5 minutes.

A solution, prepared by diluting poly(3,4-ethylenedioxythiophene)-polystyrene sulfonate (PEDOT/PSS, BAYTRON P Al 4083, produced by Bayer Co.) with pure water to reach 70% by weight, was applied onto the above supporting transparent substrate at 3,000 rpm for 30 seconds via a spin coating method so that a film was formed, followed by drying at 200° C. for one hour, whereby a 30 nm thick first positive hole transporting layer was prepared.

The substrate was moved to nitrogen atmosphere. A solution, which was prepared by dissolving 30 mg of polyvinyl carbazole (PVCz) and 3 mg of Ir-1 in 10 ml of dichloroethane, was applied onto the substrate at 600 rpm for 30 seconds via a spin coating method, and a light emitting layer was prepared.

A solution prepared by that 50 mg of (tBu)PBD was dissolved in 10 ml of methanol was applied onto the emitting layer at 1,500 rpm for 30 seconds via a spin coating method to form an electron transport layer.

Then the substrate was set in a vacuum evaporation apparatus and the pressure of the vacuum chamber was reduced to $4 \times 10^{-4}$ Pa. A cathode buffer layer of 1.0 nm of lithium fluoride and an anode of 110 nm of aluminum were vapor deposited to prepare the Organic EL Element 2-1.

The Organic EL Element 2-2 was prepared in the same way as the Organic EL Element 2-1 except that an amount of Ir-1 was modified to be 0.1 weight % based on the amount of (tBu)PBD in the electron transport layer.

The Organic EL Element 2-3 was prepared in the same way as the Organic EL Element 2-2 except that polyvinyl carbazole (PVCz) was replaced by a-42.

(Evaluation of Organic EL Elements)

Organic EL Elements 2-1, 2-2 and 2-3 prepared as above were evaluated, and the result is shown in Table 1.

(External Extraction Quantum Yield)

A constant electric current of 2.5 mA/cm$^2$ was applied to each of the prepared organic EL elements at 23° C. under an ambience of desiccated nitrogen gas, and the external extraction quantum yield (in %) was determined. Determination was also carried out by employing a spectral radiance meter CS-1000 (produced by Konica Minolta Inc.). Determination results of the external extraction quantum yield were subjected to relative comparison, with the value of Organic EL element 2-1 set at 100.

(Light Emitting Lifetime)

During driving via application of a constant electric current of 2.5 mA/cm$^2$ at 23° C. under an ambience of desiccated nitrogen gas, determined was the time which had passed until luminance decreased to one-half from that immediately after light emission (initial luminescence). The resulting value was designated as the half-decay time ($\tau 0.5$), which was employed as an index of lifetime. Determination was carried out by employing a spectral radiance meter CS-1000 (produced by Konica Minolta Inc.). Determination results of the light emitting lifetime of Organic EL Elements 1-1 to 1-6 were subjected to relative comparison, with the value of Organic EL element 2-1 set at 100.

TABLE 1

| Organic EL Element | Emitting layer | Electron transport layer | External Extraction Quantum Yield | Lifetime | Remarks |
|---|---|---|---|---|---|
| 2-1 | PVCz + Ir-1 | (tBu)PBD | 100 | 100 | Comparative Sample |
| 2-2 | pVCz + Ir-1 | (tBu)PBD + Ir-1 | 200 | 320 | Inventive Sample |
| 2-3 | a-42 + Ir-1 | (tBu)PBD + Ir-1 | 270 | 450 | Inventive Sample |

As is clearly seen from Table 1, it is clear that external extraction quantum yield and light emitting efficiency is low in Organic EL Element 2-1, and external extraction quantum yield and light emitting efficiency are enhanced in Organic EL Elements 2-2 and 2-3.

Example 3

(Preparation of Organic EL Elements 3-1 and 3-2)

A substrate (NA-45, produced by NH Techno Glass Corp.) prepared in such a manner that ITO (indium tin oxide) was applied onto a 100 mm×100 mm×1.1 mm glass substrate to form a 100 nm thick film as an anode, was subjected to patterning. Thereafter, a transparent supporting substrate provided with the above ITO transparent electrode was subjected to ultrasonic cleaning employing isopropyl alcohol, followed by drying via desiccated nitrogen gas and cleaned with UV ozone for 5 minutes.

A solution, which was prepared by diluting poly(3,4-ethylenedioxythiophene)-polystyrene sulfonate (PEDOT/PSS, BAYTRON P Al 4083, produced by Bayer Co.) with pure water to reach 70% by weight, was applied onto the above supporting transparent substrate at 3,000 rpm for 30 seconds via a spin coating method so that a film was formed, followed by drying at 200° C. for one hour, whereby a 30 nm thick first positive hole transporting layer was prepared.

The substrate was placed to nitrogen atmosphere, and a solution, which was prepared by dissolving 100 mg of a-40 and 10 mg It-15 in 10 ml of toluene, was applied onto the above first positive hole transporting layer at 1,000 rpm for 30 seconds via a spin coating method to obtain an emitting layer.

A solution prepared by that 50 mg of C-34 was dissolved in 10 ml of methanol was applied onto the emitting layer at 1,500 rpm for 30 seconds via a spin coating method to form an electron transport layer.

The resulting product was attached to a vacuum deposition apparatus. Subsequently, the pressure of the vacuum tank was reduced to 4×10$^{-4}$ Pa, and 1 nm lithium fluoride as a cathode buffer layer, and 110 nm aluminum as a cathode were deposited to form a cathode, whereby Organic EL Element 3-1 was prepared.

Organic EL Element 3-2 was prepared in the same manner as Organic EL element 3-1, except that a-40 was doped in the electron transport layer so as to have 1.0 weight %.

The external extraction quantum yield and the light emitting efficiency were measured for the organic EL elements 3-1 and 3-2 and the result is shown in Table 2.

TABLE 2

| Organic EL Element | Electron transport layer | External Extraction Quantum Yield | Light emitting Lifetime | Remarks |
|---|---|---|---|---|
| 3-1 | C-34 | 100 | 100 | Comparative Example |
| 3-2 | C-34 + a-40 | 220 | 400 | Present Invention |

Example 4

(Preparation of Organic EL Elements 4-1 and 4-2)

A substrate (NA-45, produced by NH Techno Glass Corp.) prepared in such a manner that ITO (indium tin oxide) was applied onto a 100 mm×100 mm×1.1 mm glass substrate to form a 100 nm thick film as an anode, was subjected to patterning. Thereafter, a transparent supporting substrate provided with the above ITO transparent electrode was subjected to ultrasonic cleaning employing isopropyl alcohol, followed by drying via desiccated nitrogen gas and cleaned with UV ozone for 5 minutes.

A solution, which was prepared by diluting poly(3,4-ethylenedioxythiophene)-polystyrene sulfonate (PEDOT/PSS, BAYTRON P Al 4083, produced by Bayer Co.) with pure water to reach 70% by weight, was applied onto the above supporting transparent substrate at 3,000 rpm for 30 seconds via a spin coating method so that a film was formed, followed by drying at 200° C. for one hour, whereby a 30 nm thick positive hole transporting layer was prepared.

The substrate was placed to nitrogen atmosphere, and a solution, which was prepared by dissolving 50 mg of Compound A" in 10 ml of toluene, was applied onto the above first positive hole transporting layer at 1,500 rpm for 30 seconds via a spin coating method to obtain a second positive hole transport layer.

A solution prepared by that 100 mg of a-39 and 10 mg of Ir-12 were dissolved in 10 ml of methanol was applied onto the second hole transport layer at 1,000 rpm for 30 seconds via a spin coating method to form an emitting layer.

A solution prepared by that 50 mg of C-36 was dissolved in 10 ml of methanol was applied onto the emitting layer at 1,500 rpm for 30 seconds via a spin coating method to form an electron transport layer.

The resulting product was attached to a vacuum deposition apparatus. Subsequently, the pressure of the vacuum tank was reduced to $4 \times 10^{-4}$ Pa, and 1 nm lithium fluoride as a cathode buffer layer, and 110 nm aluminum as a cathode were deposited to form a cathode, whereby Organic EL Element 4-1 was prepared.

Organic EL Element 4-2 was prepared in the same manner as Organic EL element 4-1, except that a-39 was doped in the electron transport layer so as to have 2.0 weight %.

The external extraction quantum yield and the light emitting efficiency were measured for the organic EL elements 4-1 and 4-2 and the result is shown in Table 3.

TABLE 3

Compound A"

| Organic EL Element | Electron transport layer | External Extraction Quantum Yield | Light emitting Lifetime | Remarks |
|---|---|---|---|---|
| 4-1 | C-36 | 100 | 100 | Comparative Example |
| 4-2 | C-36+ a-39 | 250 | 380 | Present Invention |

Example 5

Figure 1B:
Figure 1C:
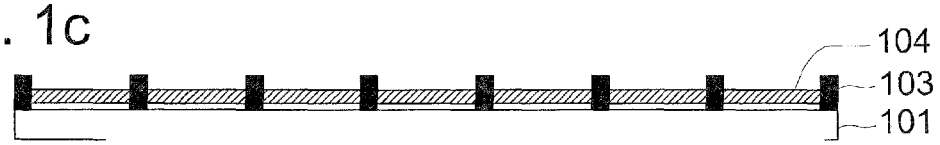
Figure 1D:
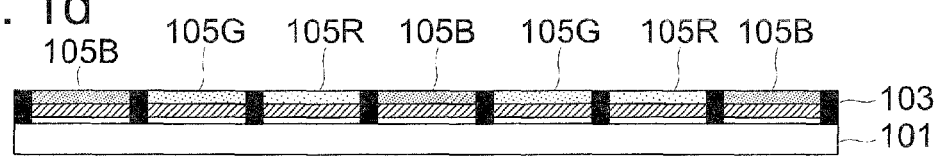
Figure 1E:
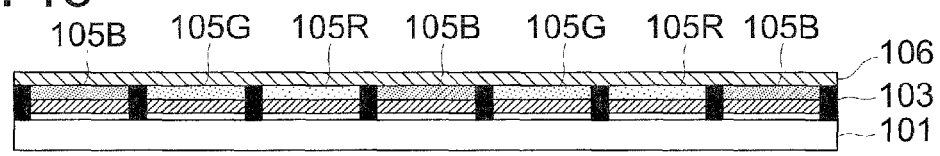

FIG. 1 is a schematic drawing of a full color display device of an organic EL element. A substrate (NA-45, produced by NH Techno Glass Corp.) prepared in such a manner that ITO (indium tin oxide) was applied onto a 100 mm×100 mm×1.1 mm glass substrate to form a 100 nm thick film as an anode, was subjected to patterning with 100 μm pitch. Partitioning wall of non-light sensitive polyimide 103 (having 20 μm width and 2.0 μm thickness) was formed via photolithography between ITO electrodes on the glass substrate. A composition for forming a positive hole injection layer of the following formulation was injected between the polyimide partitioning walls by employing an inkjet head (MJ 800C, manufactured by Seiko Epson Corporation), and was subjected to UV ray exposure for 30 second and drying process at 60° C. for 10 minutes, to obtain a hole injection layer 104 having a thickness of 40 nm.

Each of emitting layers (105B, 105G, 105R) were formed by injecting a blue light emitting layer composition, a green light emitting layer composition, and a red light emitting layer composition, each formulated below on the hole injection layer, then was subjected to UV ray exposure for 30 second and drying process at 60° C. for 10 minutes. A solution prepared by dissolving 50 mg of Compound C-19 and 0.1 mg of Compound 1-9 in 10 ml mixture solvent of toluene and methanol having mixture ratio of toluene/methanol of 95/5 was applied onto the emitting layers at 1,000 rpm for 30 seconds via a spin coating method so that a film was formed, dried at 60° C. for one hour to form an electron transport layer having thickness of 25 nm. An aluminum cathode (106) was provided via vacuum vapor method to cover the emitting layers 105 at last to produce an organic EL element.

The organic EL element thus produced above emitted blue, green and red light by applying voltage to each of electrodes, and was proved to be used as a full color display device.

| (Composition for positive hole injection layer) | |
|---|---|
| Compound A | 20 parts by weight |
| Cyclohexyl benzene | 50 parts by weight |
| Isopropyl biphenyl | 50 parts by weight |
| (Composition for blue light emitting layer) | |
| Compound 1-9 | 0.7 parts by weight |
| Ir-15 | 0.04 parts by weight |
| Cyclohexyl benzene | 50 parts by weight |
| Isopropyl biphenyl | 50 parts by weight |
| (Composition for green light emitting layer) | |
| Compound 1-9 | 0.7 parts by weight |
| Ir-1 | 0.04 parts by weight |
| Cyclohexyl benzene | 50 parts by weight |
| Isopropyl biphenyl | 50 parts by weight |
| (Composition for red light emitting layer) | |
| Compound 1-9 | 0.7 parts by weight |
| Ir-14 | 0.04 parts by weight |
| Cyclohexyl benzene | 50 parts by weight |
| Isopropyl biphenyl | 50 parts by weight |

The organic EL elements produced by employing Compounds 2-1 to 2-16 in place of Ir-15, Ir-1 and Ir-14, and Compounds 1-1 to 1-8 or 1-10 to 1-46 in place of the compound 1-9 were proved to be used as the full color display device as well.

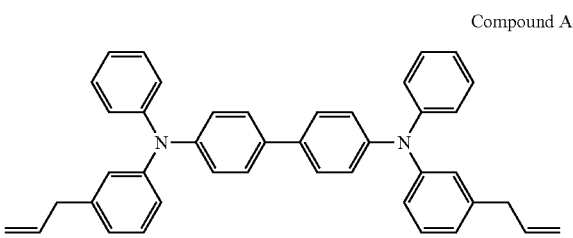

Compound A

Example 6

(Preparation of White Organic EL Element 5-1)

A substrate (NA-45, produced by NH Techno Glass Corp.) prepared in such a manner that ITO (indium tin oxide) was applied onto a 100 mm×100 mm×1.1 mm glass substrate to form a 100 nm thick film as an anode, was subjected to patterning. Thereafter, a transparent supporting substrate provided with the above ITO transparent electrode was subjected to ultrasonic cleaning employing isopropyl alcohol, followed by drying via desiccated nitrogen gas and cleaned with UV ozone for 5 minutes.

A solution, which was prepared by diluting poly(3,4-ethylenedioxythiophene)-polystyrene sulfonate (PEDOT/PSS, BAYTRON P Al 4083, produced by Bayer Co.) with pure water to reach 70% by weight, was applied onto the above supporting transparent substrate at 3,000 rpm for 30 seconds via a spin coating method so that a film was formed, followed by drying at 200° C. for one hour, whereby a 30 nm thick positive hole transporting layer was prepared.

The substrate was placed to nitrogen atmosphere, and a solution, which was prepared by dissolving 50 mg of Compound A in 10 ml of toluene, was applied onto the above first positive hole transporting layer at 1,000 rpm for 30 seconds via a spin coating method to form a layer. Then it was subjected to UV ray exposure for 180 seconds to conduct photopolymerization and crosslinking, followed by drying at 60° C. for one hour, whereby a second positive hole transport layer was prepared.

A solution prepared by that 60 mg of Compound 1-10, 3.0 mg of Compound 2-6 and 3.0 mg of Compound 2-7 were dissolved in 10 ml of methanol was applied onto the second hole transport layer at 1,000 rpm for 30 seconds via a spin coating method to form an emitting layer.

A solution prepared by that 20 mg of Compound B was dissolved in 6 ml of toluene was applied to form a layer at 1,000 rpm for 30 seconds via a spin coating method. It was subjected to UV ray exposure for 15 seconds, followed by drying at 80° C. for one hour, whereby a positive hole blocking layer was prepared.

A solution prepared by dissolving 50 mg of Compound C-19 and 0.1 mg of Compound 1-10 in 10 ml mixture solvent of toluene and methanol having mixture ratio of toluene/methanol of 95/5 was applied onto the positive hole blocking layer at 500 rpm for 30 seconds via a spin coating method so that a film was formed, dried at 60° C. for one hour to form an electron transport layer having thickness of 25 nm.

The resulting product was fixed to a substrate holder of a vacuum deposition apparatus. Subsequently, 0.5 nm lithium fluoride and 110 nm aluminum were deposited to form a cathode, whereby Organic EL Element 5-1 was prepared.

Almost white light emission was observed when electric power was applied and was proved to be used as an illumination device. It was also proved to obtain white light similarly in case of replacing to other illustrated compounds.

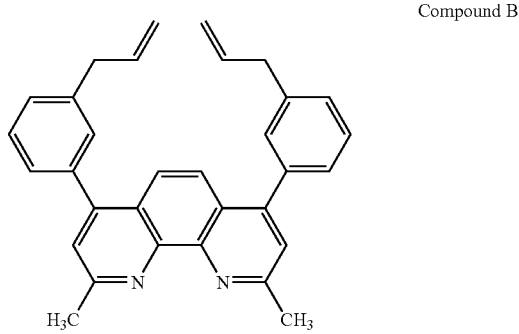

Compound B

What is claimed is:

1. An organic EL element comprising at least an anode and a cathode on a supporting substrate, and at least two layers of a first organic layer and a second organic layer between the anode and the cathode, wherein the first organic layer contains a light emitting dopant, the second organic layer contains an electron transport material and a material which composes the first organic layer, the second organic layer is formed by a coating method after forming the first organic layer, and the first organic layer contains a compound represented by Formula (a),

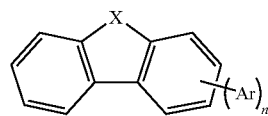

Formula (a)

wherein X is NR', O, S, CR'R" or SiR'R", wherein R' and R" is each a hydrogen atom or a substituent, Ar is an aromatic ring, and n is an integer of 0 to 4.

2. The organic EL element of claim 1, wherein the second organic layer is formed on the first organic layer by a coating method.

3. The organic EL element of claim 1, wherein the first organic layer is formed by a coating method.

4. The organic EL element of claim 1, wherein the organic EL element comprises three or more organic layers.

5. The organic EL element of claim 1, wherein the organic EL element comprises at least one of anode buffer layer.

6. The organic EL element of claim 1, wherein the emitting dopant is a phosphorescent light emitting dopant.

7. The organic EL element of claim 6, wherein the phosphorescent light emitting dopant is an iridium complex.

8. The organic EL element of claim 1, wherein the second organic layer contains an azacarbazole derivative.

9. The organic EL element of claim 1, wherein the aromatic ring represented by Ar in Formula (a) is benzene ring or an aromatic heterocyclic ring in which 3 or more rings are condensed.

10. The organic EL element of claim 1, wherein X is NR', O, or S in Formula (a).

11. The organic EL element of claim 1, wherein the first organic layer contains at least a compound having a reactive substituent or a polymer thereof.

12. The organic EL element of claim 1, wherein the material which composes the first organic layer is a phosphorescent light emitting dopant.

13. The organic EL element of claim 1, which emits white light.

14. A display device providing an organic EL element claim 1.

15. A illumination device providing an organic EL element claim 1.

* * * * *